(12) United States Patent
Raibekas et al.

(10) Patent No.: US 10,765,747 B2
(45) Date of Patent: *Sep. 8, 2020

(54) METHODS OF REDUCING AGGREGATION OF IL-1RA

(75) Inventors: Andrei Raibekas, Thousand Oaks, CA (US); Bruce Kerwin, Thousand Oaks, CA (US)

(73) Assignee: SWEDISH ORPHAN BIOVITRUM AB (PUBL), Stockholm (SE)

( * ) Notice: Subject to any disclaimer, the term of this patent is extended or adjusted under 35 U.S.C. 154(b) by 946 days.

This patent is subject to a terminal disclaimer.

(21) Appl. No.: 11/097,993

(22) Filed: Apr. 1, 2005

(65) Prior Publication Data

US 2005/0271618 A1  Dec. 8, 2005
US 2007/0098684 A9  May 3, 2007

Related U.S. Application Data

(60) Provisional application No. 60/558,879, filed on Apr. 2, 2004, provisional application No. 60/559,161, filed on Apr. 2, 2004, provisional application No. 60/601,216, filed on Aug. 12, 2004, provisional application No. 60/601,229, filed on Aug. 12, 2004.

(51) Int. Cl.

| | |
|---|---|
| A61K 38/20 | (2006.01) |
| C07K 14/54 | (2006.01) |
| C07K 14/545 | (2006.01) |
| A61K 47/02 | (2006.01) |
| A61K 47/12 | (2006.01) |
| A61K 47/26 | (2006.01) |
| A61K 33/42 | (2006.01) |
| A61K 31/7012 | (2006.01) |
| A61K 9/00 | (2006.01) |

(52) U.S. Cl.
CPC ............ *A61K 47/02* (2013.01); *A61K 9/0019* (2013.01); *A61K 31/7012* (2013.01); *A61K 33/42* (2013.01); *A61K 38/20* (2013.01); *A61K 47/12* (2013.01); *A61K 47/26* (2013.01); *C07K 14/54* (2013.01); *C07K 14/545* (2013.01); *Y02A 50/473* (2018.01)

(58) Field of Classification Search
CPC ......... A61K 47/26; A61K 33/42; A61K 31/70
See application file for complete search history.

(56) References Cited

U.S. PATENT DOCUMENTS

| | | | |
|---|---|---|---|
| 4,226,846 A * | 10/1980 | Saklad .................... | 424/1.37 |
| 4,935,343 A | 6/1990 | Allison et al. | |
| 4,968,607 A | 11/1990 | Dower et al. | |
| 5,081,228 A | 1/1992 | Dower et al. | |
| 5,180,812 A | 1/1993 | Dower et al. | |
| 5,296,592 A | 3/1994 | Dower et al. | |
| 5,319,071 A | 6/1994 | Dower et al. | |
| 5,359,032 A | 10/1994 | Dayer et al. | |
| 5,488,032 A | 1/1996 | Dower et al. | |
| 5,492,888 A | 2/1996 | Dower et al. | |
| 5,510,462 A | 4/1996 | Auron et al. | |
| 5,580,856 A * | 12/1996 | Prestrelski et al. ............. | 514/21 |
| 5,591,457 A | 1/1997 | Bolton | |
| 5,656,627 A | 8/1997 | Bemis et al. | |
| 5,914,391 A * | 6/1999 | Gerber et al. ................ | 530/385 |
| 5,980,954 A | 11/1999 | Bolton | |
| 5,985,657 A | 11/1999 | Auron et al. | |
| 6,020,152 A | 2/2000 | Tedder | |
| 6,096,728 A * | 8/2000 | Collins et al. .................. | 514/62 |
| 6,294,170 B1 | 9/2001 | Boone et al. | |
| 6,323,311 B1 | 11/2001 | Liu et al. | |
| 6,416,753 B1 | 7/2002 | Yuan et al. | |
| 6,511,665 B1 | 1/2003 | Dower et al. | |
| 6,525,102 B1 * | 2/2003 | Chen et al. .................. | 424/85.2 |
| 6,599,873 B1 | 7/2003 | Sommer et al. | |
| 6,660,843 B1 | 12/2003 | Feige et al. | |
| 7,619,066 B2 | 11/2009 | Raibekas et al. | |

FOREIGN PATENT DOCUMENTS

| | | |
|---|---|---|
| EP | 0 502 956 B1 | 4/1997 |
| JP | H08-504755 A | 5/1996 |
| JP | 2001-500472 A | 1/2001 |
| JP | 2001-500876 A | 1/2001 |
| JP | 2003-510368 A | 3/2003 |
| WO | WO 92/11359 | 7/1992 |
| WO | WO 94/06457 * | 3/1994 |
| WO | WO 94/06457 A1 | 3/1994 |
| WO | WO 96/23067 | 8/1996 |
| WO | WO 97/28828 A1 | 8/1997 |
| WO | WO 98/08969 | 3/1998 |
| WO | WO 98/11912 A1 | 3/1998 |
| WO | WO 99/36541 | 7/1999 |
| WO | WO 00/24782 A2 | 5/2000 |

(Continued)

OTHER PUBLICATIONS

Ludolph et. al. (Chem. Eur. J. 2003, 9, 3683-3691.*
Light, A., Protein Solubility, Protein Modifications and Protein Folding (1985), BioTechniques, vol. 3, No. 4, p. 298-306.*
Dixon, HBF, Perham, RN, Reversible Blocking of Amino Groups with Citraconic Anhydride (1968), Biochem. J., vol. 109, p. 312-314.*
Chang et al., Biophys. J., 1996, vol. 71(6):3399-3406.*
Necas et al., Veterinarni Medicina, 2008, vol. 53(8):397-411.*
BeMiller, J.N., 2004, "Carbohydrates", in: "Kirk-Othmer Encyclopedia of Chemical Technology", pp. 696-733.*

(Continued)

*Primary Examiner* — Xiaozhen Xie
(74) *Attorney, Agent, or Firm* — Finnegan, Henderson, Farabow, Garrett & Dunner LLP

(57) ABSTRACT

Methods of reducing aggregation of an aggregating IL-1ra comprising incubating IL-1ra with at least one accessory molecule are provided. Kits comprising IL-1ra and at least one accessory molecule are also provided. Pharmaceutical compositions comprising IL-1ra and at least one accessory molecule are also provided.

7 Claims, 24 Drawing Sheets

Specification includes a Sequence Listing.

(56) References Cited

FOREIGN PATENT DOCUMENTS

| WO | WO 00/24782 A3 | 5/2000 |
| --- | --- | --- |
| WO | WO 01/02571 A2 | 1/2001 |
| WO | WO 01/02571 A3 | 1/2001 |
| WO | WO 01/19390 A1 | 3/2001 |
| WO | WO 01/24814 A1 | 4/2001 |
| WO | WO 01/25435 A2 | 4/2001 |
| WO | WO 01/25435 A3 | 4/2001 |
| WO | WO 02/36152 A1 | 5/2002 |
| WO | WO 02/062375 A1 | 8/2002 |
| WO | WO 2004/022718 A2 | 3/2004 |
| WO | WO 2004/022718 A3 | 3/2004 |
| WO | WO 2004/071439 * | 8/2004 |

OTHER PUBLICATIONS

Bottomley et al., "The citrate ion increases the conformational stability of $\alpha_1$-antitrypsin," Biochem. Biophys. Acta, 1481:11-17 (2000).
Chen et al., "Strategies to suppress aggregation of recombinant keratinocyte growth factor during liquid formulation development," J. Pharm. Sci., 83:1657-1661 (1994).
Dower et al., "The interleukin-1 receptor," Immunology Today, 8(2):46-51 (1987).
Evans et al., "Mapping receptor binding sites in interleukin (IL)-1 receptor antagonist and IL-1β by site-directed mutagenesis," J. Biol. Chem., 270:11477-11483 (1995).
Gallivan et al., "Cation-π interactions in structural biology," Proc. Natl. Acad. Sci. USA, 96:9459-9464 (1999).
MacLean et al., "Stabilization of proteins by low molecular weight multi-ions," J. Pharm. Sci., 91:2220-2229 (2002).
Schreuder et al., "Refined crystal structure of the interleukin-1 receptor antagonist," Eur. J. Biochem., 227:838-847 (1995).
Sims et al., "Cloning the interleukin 1 receptor from human T cells," Proc. Natl. Acad. Sci. USA, 86:8946-8950 (1989).
Smith et al., "A single amino acid difference between human and monkey interleukin (IL)-1β dictates effective binding to soluble type II IL-1 receptor," J. Biol. Chem., 277:47619-47625 (2002).
Van den Burg et al., "Selection of mutations for increased protein stability," Curr. Opin. Biotech., 13:333-337 (2002).
Vigers et al., "X-ray structure of interleukin-1 receptor antagonist at 2.0 Å resolution," J. Biol. Chem., 269:12874-12879 (1994).
Vigers et al., "Crystal structure of the type-I interleukin-1 receptor complexed with interleukin-1β," Nature, 368:190-194 (1997).
Chang et al., "Development of a stable freeze-dried formulation of recombinant human interleukin-1 receptor antagonist," Pharmaceutical Research, 13:243-249 (1996).
Chang et al., "Physical factors affecting the storage stability of freeze-dried interleukin-1 receptor antagonist: glass transition and protein conformation," Archives of Biochemistry and Biophysics, 331:249-258 (1996).
PCT Notification of Transmittal of the International Search Report and the Written Opinion of the International Searching Authority, or the Declaration, dated May 9, 2006, for Application No. PCT/US2005/011332.
Examiner's First Report for Australian Patent Application No. 2005231822, dated Oct. 29, 2009 (2 pages).
Letter and enclosure submitted in European Patent Application No. 05733155.5, dated May 29, 2007 (7 pages).
Communication pursuant to Article 94(3) EPC for European Patent Application No. 05733155.5, dated Jul. 29, 2009 (4 pages).
Non-final Office Action for U.S. Appl. No. 11/097,453, dated Oct. 31, 2007 (22 pages).
Amendment and Response for U.S. Appl. No. 11/097,453, filed Jan. 30, 2008 (31 pages).
Final Office Action for U.S. Appl. No. 11/097,453, dated Apr. 30, 2008 (14 pages).
Amendment and Response After Final for U.S. Appl. No. 11/097,453, filed Oct. 30, 2008 (35 pages).
Advisory Action for U.S. Appl. No. 11/097,453, dated Nov. 24, 2008 (3 pages).
Interview Summary for U.S. Appl. No. 11/097,453, dated Dec. 15, 2008 (2 pages).
Amendment and Response for U.S. Appl. No. 11/097,453, filed Feb. 27, 2009 (37 pages).
Request for Continued Examination for U.S. Appl. No. 11/097,453, filed Feb. 27, 2009 (1 page).
Submission of Terminal Disclaimer for U.S. Appl. No. 11/097,453, filed Jun. 8, 2009 (16 pages).
Notice of Allowance and Fee(s) due and Notice of Allowability with attachments for U.S. Appl. No. 11/097,453, dated Jul. 6, 2009 (10 pages).
Official Action from the Instituto Mexicano de la Propiedad Industrial, dated Jun. 30, 2010, in Mexican Patent Appln. No. PA/a/2006 010352 (2 pages); and Translation of the Requirements Stated by the Examiner for Mexican Patent Application No. PA/a/2006/010352 (3 pages).
Response to the Official Communication dated Jul. 29, 2009, filed Apr. 8, 2010, for European Patent Application No. 05733155.5 (17 pages).
Official Action, dated Jan. 12, 2011, in Canadian Patent Application No. 2,557,910, by Tung Siu, pp. 1-3.
Examiner's Report No. 2, dated Dec. 16, 2010, in Australian Patent Application No. 2005231822, signed by Suzanne Pietersz, pp. 1-2.
Response dated Nov. 29, 2010, in Australian Patent Application No. 2005231822, signed by Grant Shoebridge, pp. 1-3.
First Statement of Proposed Amendments—Section 104(1), dated Nov. 29, 2010, in Australian Patent Application No. 2005231822, signed by Grant Shoebridge, p. 1, and 19 attached pages.
Notice of Rejection (1st Official Action) dated Feb. 8, 2011, for Japanese Patent Application No. 2007-506351, including translation (9 pages).
Official Action from the Instituto Mexicano de la Propiedad Industrial, dated Mar. 16, 2011, in Mexican Patent Appln. No. PA/a/2006/010352 and Translation of the Requirements Stated by the Examiner for Mexican Patent Application No. PA/a/2006/010352 (3 pages).
Examiner's report No. 3, dated Apr. 6, 2011, for Australian Patent Application No. 2005231822 (2 pages).
Respuesta al Oficio de Requisitos, filed Nov. 4, 2010, for Mexican Patent Appln. No. PA/a/2006 010352 (13 pages); and an English translation of the claims (8 pages).
Notice of Rejection (2nd Official Action) dated Oct. 11, 2011, for Japanese Patent Application No. 2007-506351, including translation (11 pages).
Argument and Amendment, dated Apr. 11, 2012, for Japanese Patent Application No. 2007-506351, including translation (19 pages).
Communication pursuant to Article 94(3) EPC dated Jan. 24, 2012, for European Patent Application No. 05733155.5 (5 pages).
Official Action dated Dec. 5, 2011, for Mexican Patent Application No. PA/a/2006/010352, including translation ( 5pages).
Response to the Official Communication dated Jan. 24, 2012, filed Sep. 26, 2012, for European Patent Application No. 05733155.5 (14 pages).
Examiner's Decision of Rejection, dated Sep. 25, 2012, for Japanese Patent Application No. 2007-506351, including translation (6 pages).
Response filed Apr. 13, 2012, for Mexican Patent Application No. PA/a/2006/010352, including translation of pending claims (16 pages).
Interrogation by the Chief Appeal-Examiner with Re-examination Report, dated Jan. 28, 2014, for Japanese Patent Application No. 2007-506351, including translation (6 pages).
Notice of Rejection (1st Official Action), dated May 13, 2014, for Japanese Patent Application No. 2013-001368 (12 pages).
Response filed Nov. 5, 2014, for Japanese Patent Application No. 2013-001368 (11 pages).
Notice of Rejection (2nd Official Action) dated Jun. 2, 2015, for Japanese Patent Application No. 2013-001368 (7 pages).
Argument and Amendment filed Aug. 31, 2015, for Japanese Patent Application No. 2013-001368 (12 pages).
Notice of Rejection (1st Official Action) dated Oct. 28, 2015, for Japanese Patent Application No. 2014-224940 and English translation (7 pages).

(56) References Cited

OTHER PUBLICATIONS

Decision of Dismissal of an Argument dated Sep. 29, 2015, for Japanese Patent Application No. 2013-011368 and English translation (6 pages).
Sen-i Gakkaisi, 1981, 37(12), pp. 436-443 (11 pages).
Japanese Office Action in Japanese Patent Application No. 2013-11368, dated Jan. 24, 2017; English-language translation included; (13 pgs.).
Summons to attend oral proceedings pursuant to Rule 175(1) EPC in EP Patent Application No. 05733155.5, dated Feb. 13, 2017; (6 pgs.).
Gray et al., "Effect of citraconylation on the thermal aggregation of human serum albumin," Int. J. Biol. Macromol., vol. 2, pp. 2-6 (1980).

* cited by examiner

IL-1ra aggregation at 39°C (405 nm)

RP HPLC of IL-1ra, NBD-X – labeled at pH 6.5

FIG. 5

```
         10        20    ↓   30        40        50        60
GAATTCCGGGCTGCAGTCACAGAATGGAAATCTGCAGAGGCCTCCGCAGTCACCTAATCA
                        M  E  I  C  R  G  L  R  S  H  L  I 70        80        90       1↓00       110       120
CTCTCCTCCTCTTCCTGTTCCATTCAGAGACGATCTGCCGACCCTCTGGGAGAAAATCCA
 T  L  L  L  F  L  F  H  S  E  T  I  C (R) P  S  G  R  K  S 130       140       150       160       170       180
GCAAGATGCAAGCCTTCAGAATCTGGGATGTTAACCAGAAGACCTTCTATCTGAGGAACA
 S  K  M  Q  A  F  R  I  W  D  V  N  Q  K  T  F  Y  L  R  N 190       200       210       220       230       240
ACCAACTAGTTGCTGGATACTTGCAAGGACCAAATGTCAATTTAGAAGAAAAGATAGATG
 N  Q  L  V  A  G  Y  L  Q  G  P  N  V  N  L  E  E  K  I  D 250       260       270       280       290       300
TGGTACCCATTGAGCCTCATGCTCTGTTCTTGGGAATCCATGGAGGGAAGATGTGCCTGT
 V  V  P  I  E  P  H  A  L  F  L  G  I  H  G  G  K  M  C  L 310       320       330       340       350       360
CCTGTGTCAAGTCTGGTGATGAGACCAGACTCCAGCTGGAGGCAGTTAACATCACTGACC
 S  C  V  K  S  G  D  E  T  R  L  Q  L  E  A  V  N  I  T  D 370       380       390       400       410       420
TGAGCGAGAACAGAAAGCAGGACAAGCGCTTCGCCTTCATCCGCTCAGACAGTGGCCCCA
 L  S  E  N  R  K  Q  D  K  R  F  A  F  I  R  S  D  S  G  P 430       440       450       460       470       480
CCACCAGTTTTGAGTCTGCCGCCTGCCCCGGTTGGTTCCTCTGCACAGCGATGGAAGCTG
 T  T  S  F  E  S  A  A  C  P  G  W  F  L  C  T  A  M  E  A 490       500       510       520       530       540
ACCAGCCCGTCAGCCTCACCAATATGCCTGACGAAGGCGTCATGGTCACCAAATTCTACT
 D  Q  P  V  S  L  T  N  M  P  D  E  G  V  M  V  T  K  F  Y

550      ↓560       570       580       590       600
TCCAGGAGGACGAGTAGTACTGCCCAGGCCTGCTGTTCCATTCTTGCATGGCAAGGACTG
 F  Q  E  D  E  *
```

| [Pyrophosphate] Xtotal | [Citrate]total Ltotal | [Citrate-IL-1ra] PL | [IL-1ra]total Ptotal | [IL-1ra]free Pfree | [Citrate]free Lfree | Delta [Citrate-IL-1ra] as [Pyrophosphate] increases DeltaPL | [Pyrophosphate]free Xfree | Kd, App for Citrate |
|---|---|---|---|---|---|---|---|---|
| 0.000 | 10.000 | 1.129 | 1.750 | 0.621 | 8.871 | 0.000 | 0.000 | 4.877 |
| 5.000 | 10.000 | 0.837 | 1.750 | 0.913 | 9.163 | 0.292 | 4.708 | 9.986 |
| 10.000 | 10.000 | 0.703 | 1.790 | 1.087 | 9.297 | 0.426 | 9.574 | 14.376 |
| 20.000 | 10.000 | 0.433 | 1.790 | 1.357 | 9.567 | 0.696 | 19.304 | 29.941 |

Competitive Binding with Pyrophosphate

Slope/intercept = $1/K^d_X$
$K^d_X$ for pyrophosphate = 2.994mM

FIGURE 23

```
  1                                                    cat 4 atgcgaccgtccggccgtaagagctccaaaatgcaggctttccgt
  1 M   R   P   S   G   R   K   S   S   K   M   Q   A   F   R 49 atctgggacgttaaccagaaaaccttctacctgcgcaacaaccag
 16 I   W   D   V   N   Q   K   T   F   Y   L   R   N   N   Q 94 ctggttgctggctacctgcagggtccgaacgttaacctggaagaa
 31 L   V   A   G   Y   L   Q   G   P   N   V   N   L   E   E 139 aaaatcgacgttgtaccgatcgaaccgcacgctctgttcctgggt
 46 K   I   D   V   V   P   I   E   P   H   A   L   F   L   G 184 atccacggtggtaaaatgtgcctgagctgcgtgaaatctggtgac
 61 I   H   G   G   K   M   C   L   S   C   V   K   S   G   D 229 gaaactcgtctgcagctggaagcagttaacatcactgacctgagc
 76 E   T   R   L   Q   L   E   A   V   N   I   T   D   L   S 274 gaaaaccgcaaacaggacaaacgtttcgcattcatccgctctgac
 91 E   N   R   K   Q   D   K   R   F   A   F   I   R   S   D 319 agcggcccgaccaccagcttcgaatctgctgcttgcccgggttgg
106 S   G   P   T   T   S   F   E   S   A   A   C   P   G   W 364 ttcctgtgcactgctatggaagctgaccagccggtaagcctgacc
121 F   L   C   T   A   M   E   A   D   Q   P   V   S   L   T 409 aacatgccggacgaaggcgtgatggtaaccaaattctacttccag
136 N   M   P   D   E   G   V   M   V   T   K   F   Y   F   Q 454 gaagacgaataatgggaagctt 465          SEQ ID NO: 4
151 E   D   E   *                      SEQ ID NO: 5
```

FIGURE 24

```
  1 MALETICRPSGRKSSKMQAFRIWDVNQKTFYLRNNQLVAGYLQGPNVNLE  50
 51 EKIDVVPIEPHALFLGIHGGKMCLSCVKSGDETRLQLEAVNITDLSENRK 100
101 QDKRFAFIRSDSGPTTSFESAACPGWFLCTAMEADQPVSLTNMPDEGVMV 150
151 TKFYFQEDE 159       SEQ ID NO: 6
```

METHODS OF REDUCING AGGREGATION OF IL-1RA

This application claims the benefit of U.S. Provisional Application No. 60/558,879, filed Apr. 2, 2004, U.S. Provisional Application No. 60/559,161, filed Apr. 2, 2004, U.S. Provisional Application No. 60/601,216, filed Aug. 12, 2004, and U.S. Provisional Application No. 60/601,229, filed Aug. 12, 2004. U.S. Provisional Application Nos. 60/558,879, 60/559,161, 60/601,216, and 60/601,229 are incorporated by reference herein for any purpose.

FIELD

The present invention relates to methods of reducing aggregation of an aggregating interleukin-1 receptor antagonist (IL-1ra). The present invention also relates to methods of improving drug formulations comprising reducing aggregation of IL-1ra. The present invention also relates to methods of treating diseases using IL-1ra whose aggregation has been reduced. Finally, the present invention relates to compositions and kits comprising an IL-1ra whose aggregation has been reduced.

BACKGROUND

Interleukin-1 alpha (IL-1α), interleukin-1 beta (IL-1β), and interleukin-1 receptor antagonist (IL-1ra) each binds to the type 1 IL-1 receptor (IL-1-RI), which is found on the surface of certain cell types. IL-1α and IL-1β have physiological effects on a number of different target cells, including certain cells that are involved in the inflammatory and immune responses. IL-1ra, in contrast, binds to IL-1RI, but does not elicit comparable downstream biological responses. Rather, IL-1ra competitively inhibits IL-1α and IL-1β binding to IL-1RI. Anakinra, an *E. coli*-produced version of IL-1ra, is marketed for treatment of rheumatoid arthritis.

SUMMARY

In certain embodiments, a method of reducing aggregation of an aggregating interleukin-1 receptor antagonist (IL-1ra) is provided. In certain embodiments, the method comprises incubating IL-1ra with at least one accessory molecule.

In certain embodiments, a method of preparing an interleukin-1 receptor antagonist (IL-1ra) drug formulation is provided. In certain embodiments, the method comprises incubating the aggregating IL-1ra with at least one accessory molecule. In certain embodiments, aggregation is reduced.

In certain embodiments, a method of treating a patient is provided. In certain embodiments, a method of treating a patient having arthritis is provided. In certain embodiments, a method of treating a patient having rheumatoid arthritis is provided. In certain embodiments, a method of treating a patient having osteoarthritis is provided. In certain embodiments, a method of treating a patient having at least one of Crohn's disease, ulcerative colitis, glomerulonephritis, or leukemia is provided. In certain embodiments, a method of treating a patient having an adverse effect of IL-1 is provided. In certain embodiments, the method of treating a patient comprises administering to the patient a composition comprising (i) a therapeutically effective amount of an aggregating interleukin-1 receptor antagonist (IL-1ra) and (ii) at least one accessory molecule.

In certain embodiments, kits are provided. In certain embodiments, a kit comprises an aggregating interleukin-1 receptor antagonist (IL-1ra) and at least one accessory molecule.

In certain embodiments, pharmaceutical compositions are provided. In certain embodiments, pharmaceutical compositions comprise an aggregating interleukin-1 receptor antagonist (IL-1ra) and at least one accessory molecule.

In certain embodiments, at least one accessory molecule is at a concentration that reduces aggregation of an aggregating IL-1ra. In certain embodiments, at least one accessory molecule is at a concentration that reduces the rate of aggregation of an aggregating IL-1ra. In certain embodiments, at least one accessory molecule is selected from a sugar and a multiple-charge anion. In certain embodiments, at least one accessory molecule is a multiple-charge anion. In certain embodiments, at least one accessory molecule is 1 to 20 mM pyrophosphate. In certain embodiments, at least one accessory molecule is 1 to 20 mM citrate. In certain embodiments, at least one accessory molecule is at least one sugar. In certain embodiments, at least one of said sugars is glycerol, sorbitol, or sucrose. In certain embodiments, at least one of such sugars is at a concentration of from 1 to 3 percent.

In certain embodiments, at least one accessory molecule is selected from a lysine-reactive accessory molecule and an arginine-reactive accessory molecule. In certain embodiments, at least one accessory molecule is selected from 6-(N-(7-nitrobenz-2-oxa-1,3-diazol-4-yl)amino)hexanoic acid (NBD-X), methyl acetyl phosphate (MAP), and citraconic anhydride.

BRIEF DESCRIPTION OF THE FIGURES

FIG. 5 shows the nucleotide sequence (SEQ ID NO: 1) and amino acid sequence (SEQ ID NO: 2) of precursor human IL-1ra, which includes a secretory leader sequence.

FIG. 6 shows the amino acid sequence of human IL-1ra lacking the secretory leader sequence (SEQ ID NO: 3). The dot (•) indicates the lysine at position 93. The plus (+) indicates the arginine at position 97. The locations of tryptophan-16 (Δ) and tyrosine-34 (○) are also indicated.

FIG. 16A shows a reproduction of the chromatograms from FIG. 13. FIG. 16B shows the results of deconvoluting each chromatogram from FIG. 16A. FIG. 16C shows a plot of the integration of each of the deconvoluted peaks from FIG. 16B versus time.

FIG. 23 shows the nucleotide sequence (SEQ ID NO: 4) and amino acid sequence (SEQ ID NO: 5) of an exemplary IL-1ra.

FIG. 24 shows the amino acid sequence of an exemplary IL-1ra, referred to as icIL-1ra (SEQ ID NO: 6). SEQ ID NO: 6 has the same sequence as SEQ ID NO: 3, but with an additional 7 amino acids at the N-terminus.

DETAILED DESCRIPTION OF CERTAIN EXEMPLARY EMBODIMENTS

Figure 1:
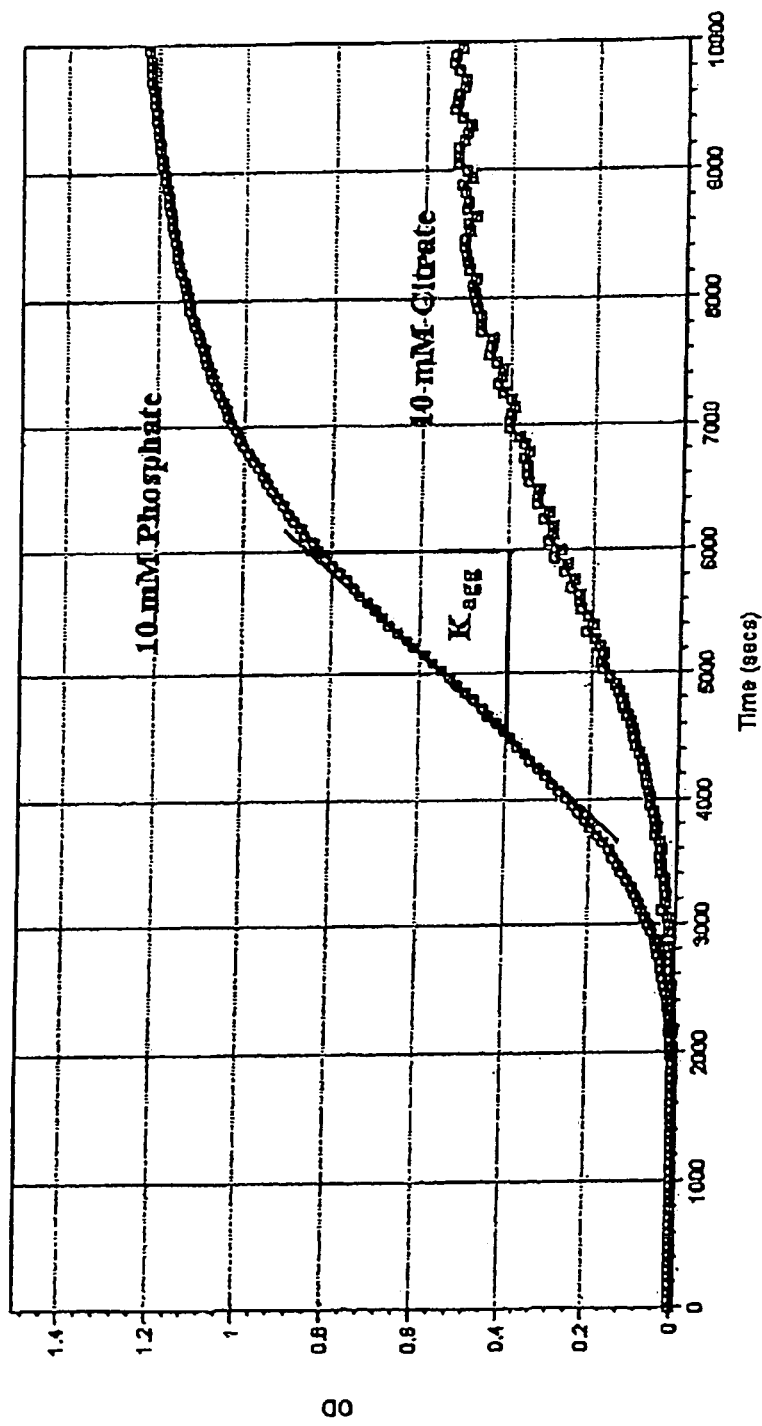
FIG. 1 shows the IL-1ra wild-type protein aggregation profile over time in either PSE (10 mM phosphate, pH 6.5, 140 mM NaCl, 0.5 mM EDTA) or CSE (10 mM citrate, pH 6.5, 140 mM NaCl, 0.5 mM EDTA) discussed in Example 2.

The section headings used herein are for organizational purposes only and are not to be construed as limiting the subject matter described. All references cited in this application are expressly incorporated by reference herein for any purpose.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

In various embodiments, standard techniques may be used for recombinant DNA, oligonucleotide synthesis, tissue culture, transformation and transfection. In various embodiments, enzymatic reactions and purification techniques may be performed according to manufacturer's specifications or as commonly accomplished in the art or as described herein. In various embodiments, techniques and procedures may be generally performed according to conventional methods known in the art and as described in various general and more specific references that are cited and discussed throughout the present specification and/or that are known to one skilled in the art. See e.g., Sambrook et al. Molecular Cloning: A Laboratory Manual (2d ed., Cold Spring Harbor Laboratory Press, Cold Spring Harbor, N.Y. (1989). Unless specific definitions are provided, the nomenclatures utilized in connection with, and the laboratory procedures and techniques of, analytical chemistry, synthetic organic chemistry, and medicinal and pharmaceutical chemistry described herein are those known and commonly used in the art. In various embodiments, standard techniques may be used for chemical syntheses, chemical analyses, pharmaceutical preparation, formulation, delivery, and treatment of patients. In certain embodiments, where an amino acid is "replaced" with another amino acid, that replacement may be done recombinantly, e.g., by mutating the codon in the polynucleotide that encodes the amino acid to the codon that encodes another amino acid. In certain embodiments, mutating the codon may be done by any method known in the art.

Definitions

As utilized in accordance with the present disclosure, the following terms, unless otherwise indicated, shall be understood to have the following meanings:

The term "isolated polynucleotide" shall mean a polynucleotide of genomic, cDNA, or synthetic origin, or some combination thereof, which (1) is not associated with at least a portion of a polynucleotide in which it is found in nature, or (2) is linked to a polynucleotide to which it is not linked in nature, or (3) does not occur in nature.

The term "operably linked" refers to components that are in a relationship permitting them to function in their intended manner. For example, a control sequence "operably linked" to a coding sequence is ligated in such a way that expression of the coding sequence is achieved under conditions compatible with the operation of the control sequences.

The term "control sequence" refers to polynucleotide sequences which may effect the expression and processing of coding sequences to which they are ligated. The nature of such control sequences may differ depending upon the host organism. According to certain embodiments, control sequences for prokaryotes may include promoters, ribosomal binding sites, and transcription termination sequences. According to certain embodiments, control sequences for eukaryotes may include promoters and transcription termination sequence. In certain embodiments, "control sequences" can include leader sequences and/or fusion partner sequences.

The term "polynucleotide" means a polymeric form of nucleotides having naturally occurring and/or modified ribonucleotides and/or deoxyribonucleotides which are linked together by naturally occurring and/or non-naturally occurring linkages. In certain embodiments, a polynucleotide is least 10 bases in length. The term includes single and double stranded forms of DNA/RNA, and DNA/RNA hybrid, or modified forms thereof.

The term "oligonucleotide" includes polymers having naturally occurring and/or modified ribonucleotides and/or deoxyribonucleotides, which are linked together by naturally occurring and/or non-naturally occurring linkages. Oligonucleotides are a subset of polynucleotides and generally comprise about 200 bases or fewer. In certain embodiments, oligonucleotides are about 10 to about 60 bases in length. In certain embodiments, oligonucleotides are 12, 13, 14, 15, 16, 17, 18, 19, 20, or 21 to 40 bases in length. Oligonucleotides may be single stranded or double stranded. Oligonucleotides may be sense or antisense oligonucleotides.

The term "naturally occurring nucleotides" includes deoxyribonucleotides and ribonucleotides. The term "modified nucleotides" includes nucleotides with modified or substituted sugar groups and/or modified or substituted nucleotide base groups and the like. The terms "oligonucleotide linkage" and "polynucleotide linkage" include linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. Nucl. Acids Res. 14:9081 (1986); Stec et al. J. Am. Chem. Soc. 106:6077 (1984); Stein et al. Nucl. Acids Res. 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). In certain embodiments, an oligonucleotide or polynucleotide may include a label.

The term "naturally occurring" as applied to an object refers to an object that can be found in nature. For example, a polypeptide or polynucleotide sequence that is present in an organism (including viruses) that can be isolated from a source in nature and which has not been modified by man in the laboratory or otherwise is naturally occurring.

The term "isolated protein" means a protein made by synthetic means or a protein encoded by genomic DNA, cDNA, RNA, or other polynucleotide, which (1) is free, of at least some proteins with which it would normally be found; or (2) is essentially free of other proteins from the same source, e.g., from the same species; or (3) is expressed by a cell from a different species; or (4) does not occur in nature. In the polypeptide notation used herein, the left-hand direction is the amino-terminal direction and the right-hand direction is the carboxy-terminal direction, in accordance with standard usage and convention, unless specifically indicated otherwise.

Similarly, unless specifically indicated otherwise, the left-hand end of single-stranded polynucleotide sequences is the 5' end; the left-hand direction of double-stranded polynucleotide sequences is referred to as the 5' direction. The direction of 5' to 3' addition to nascent RNA transcripts is referred to as the transcription direction; sequence regions on the DNA strand that are 5' to the 5' end of the RNA transcript are referred to as "upstream sequences" and are "upstream of the coding region"; sequence regions on the DNA strand that are 3' to the 3' end of the RNA transcript are referred to as "downstream sequences" and are "downstream of the coding region".

As used herein, the terms "label" or "labeled" refer to the presence of a detectable moiety. A detectable moiety may be incorporated during synthesis of a polynucleotide or polypeptide or may be attached, either covalently or non-covalently, after synthesis. Labeling may be, e.g., incorporation of a radiolabeled amino acid, attachment of biotin moieties that can be detected with labeled avidin (e.g., streptavidin containing a fluorescent moiety or enzymatic activity that can be detected by optical or colorimetric methods). In certain embodiments, the label or detectable moiety can be therapeutic. Various methods of labeling polypeptides and/or polynucleotides are known in the art. Examples of labels for polypeptides and/or polynucleotides include, but are not limited to: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent labels, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce the potential for steric hindrance.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)). Stereoisomers (e.g., D-amino acids) of the twenty conventional amino acids, unnatural amino acids, such as α-, α-disubstituted amino acids, N-alkyl amino acids, lactic acid, and other unconventional amino acids, may also be suitable components for polypeptides of the present invention. Non-limiting exemplary unconventional amino acids include 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids.

A skilled artisan will be able to identify suitable variants of a polypeptide with well-known techniques. In certain embodiments, one skilled in the art may identify suitable regions of a polypeptide that may be changed without destroying activity by targeting regions not believed to be important for activity. In certain embodiments, one can identify residues and portions of a polypeptide that are conserved among similar polypeptides. In certain embodiments, even areas that may be important for biological activity or for structure may be amenable to conservative amino acid substitutions without destroying the biological activity or without adversely affecting the polypeptide structure.

Additionally, in certain embodiments, one skilled in the art can review structure-function studies and identify residues in similar polypeptides that are important for activity or structure. In view of such a comparison, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can analyze the three-dimensional structure and amino acid sequence in relation to known structures in similar polypeptides. Moreover, in certain embodiments, one skilled in the art may generate test variants containing a single amino acid substitution at each desired amino acid residue. In certain embodiments, the variants can then be screened using activity assays known to those skilled in the art. Such variants could be used to gather information about suitable variants. For example, in certain embodiments, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

In certain embodiments, deletions, insertions, and/or substitutions (individually or collectively referred to as "variant(s)") are made within the amino acid sequence of a IL-1ra wild-type protein. As used herein, "IL-1ra wild-type protein" refers to a protein having the amino acid sequence of SEQ ID NO: 3, optionally having an additional methionine residue at its N-terminus, such that the N-terminal sequence is MRPSGR . . . . The therapeutic protein having the generic name "anakinra" falls within this definition of IL-1ra wild-type protein. Anakinra has the sequence of SEQ ID NO: 5, which is identical to SEQ ID NO: 3, but with an N-terminal methionine. In certain embodiments, alterations to the IL-1ra wild-type protein, such as chemical or enzymatic modification, are made after translation or synthesis of the protein. Such altered IL-1ra proteins are individually or collectively referred to as "derivative(s)". The term IL-1ra encompasses IL-1ra wild-type proteins, as well as naturally occurring and non-naturally occurring IL-1ra variants and derivatives that have antagonist activity for the IL-1ra receptor.

In certain embodiments, an "amino acid that does not have a positive charge" is selected from alanine, cysteine, aspartic acid, glutamic acid, phenylalanine, glycine, histidine, isoleucine, leucine, methionine, asparagine, proline, glutamine, serine, threonine, valine, tryptophan, and tyrosine. Amino acids that do not have a positive charge also include, but are not limited to, unconventional amino acids that do not have a positive charge. One skilled in the art can determine whether or not a particular amino acid variant has a positive charge when incorporated into a polypeptide.

In certain embodiments, an "amino acid that does not have a charge" is selected from alanine, cysteine, phenylalanine, glycine, histidine, isoleucine, leucine, methionine, asparagine, proline, glutamine, serine, threonine, valine, tryptophan, and tyrosine. Amino acids that do not have a charge also include, but are not limited to, unconventional amino acids that do not have a charge. One skilled in the art can determine whether or not a particular unconventional amino acid variant has a charge when incorporated into a polypeptide.

In certain embodiments, a "polar amino acid that does not have a charge" is selected from cysteine, glycine, glutamine, asparagine, serine, threonine, and tyrosine. Polar amino acids that do not have a charge also include, but are not limited to, unconventional amino acids that are polar but do not have a charge. One skilled in the art can determine whether or not a particular unconventional amino acid variant is polar and whether it has a charge when incorporated into a polypeptide.

In certain embodiments, a "non-aromatic amino acid" is selected from alanine, arginine, cysteine, aspartic acid, glutamic acid, glycine, histidine, isoleucine, leucine, lysine, methionine, asparagine, proline, glutamine, serine, threonine, and valine. Non-aromatic amino acids also include, but are not limited to, unconventional amino acids that are not aromatic. One skilled in the art can determine whether or not a particular unconventional amino acid variant is aromatic when incorporated into a polypeptide.

The term "cation-pi interaction" refers to a non-covalent interaction between a cationic amino acid and an aromatic amino acid. In certain embodiments, the cationic amino acid may be lysine. In certain embodiments, the cationic amino acid may be arginine. In certain embodiments, the aromatic amino acid may be phenylalanine. In certain embodiments, the aromatic amino acid may be tyrosine. In certain embodiments, the aromatic amino acid may be tryptophan. The cation-pi interaction may be within a single polypeptide (i.e., intramolecular) or the cation-pi interaction maybe between two or more polypeptides (i.e., intermolecular).

Figure 2:
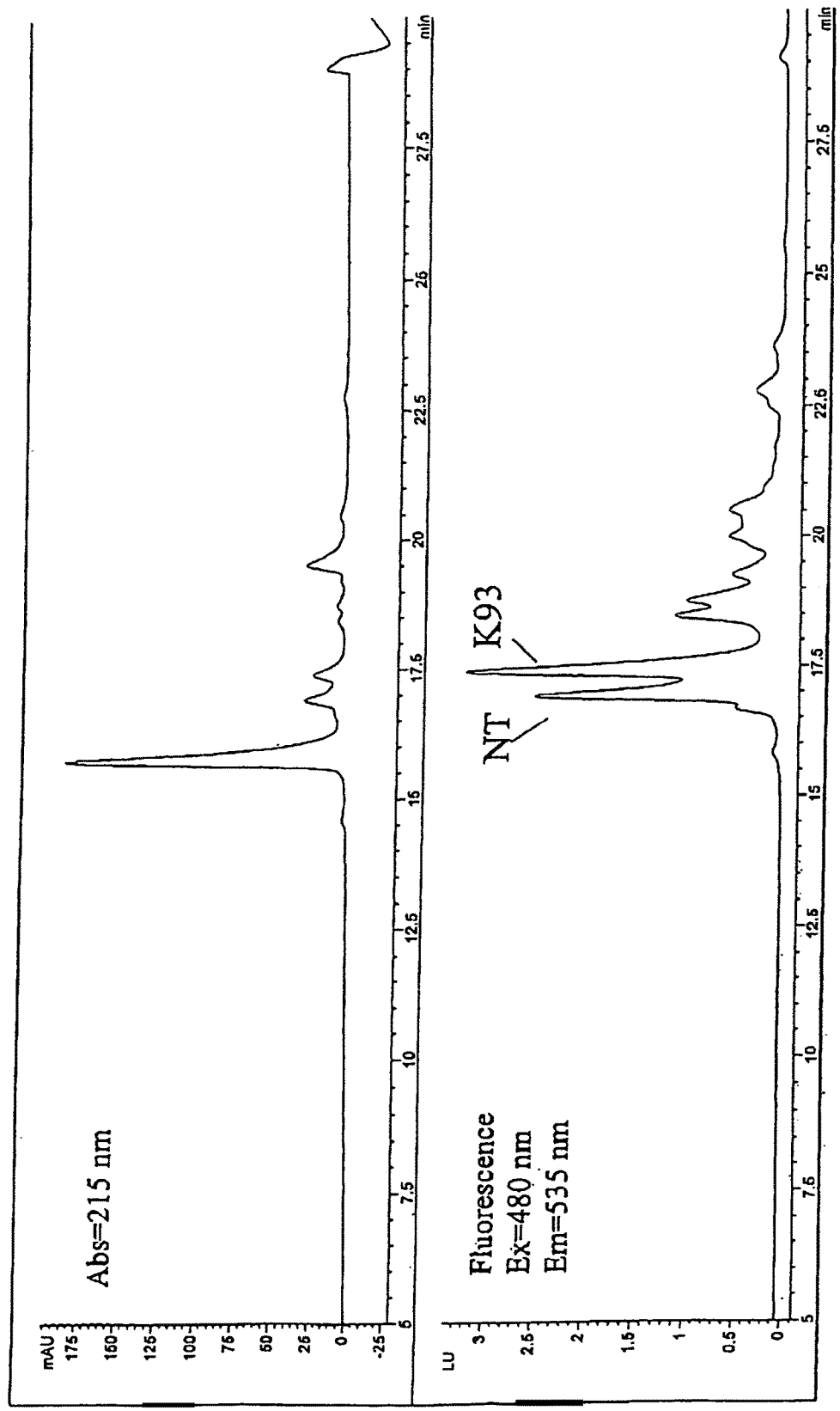
FIG. 2 shows the reverse-phase high performance liquid chromatography (RP-HPLC) of IL-1ra wild-type protein derivatized with NBD-X discussed in Example 3. The upper panel shows the absorbance of NBD-X labeled IL-1ra at 215 nm. The lower panel shows the fluorescent emission at 535 nm following excitation at 480 nm.

In certain embodiments, certain amino acid residues of IL-1ra are involved in a cation-pi interaction. FIG. 1 shows an x-ray crystal structure of IL-1ra. The crystal structure was prepared using a 1 ILR.pdb file and Vector NTI 3D Molecular Viewer (InforMax). IL-1ra crystallized as an asymmetric dimer. See, e.g., Vigers et al., *J. Biol. Chem.*, 269: 12874-12879 (1994). FIG. 2 shows a portion of the crystal structure of FIG. 1. In that crystal structure, lysine-93 on one IL-1ra subunit appears to be involved in a cation-pi interaction with tryptophan-16 on the other IL-1ra subunit. Similarly, arginine-97 on one IL-1ra subunit appears to be involved in a cation-pi interaction with tyrosine-34 on the other IL-1ra subunit.

The term "polypeptide fragment" as used herein refers to a polypeptide that has an amino-terminal and/or a carboxy-terminal deletion. In certain embodiments, fragments are at least 5 to 201 amino acids long. It will be appreciated that in certain embodiments, fragments are at least 5, 6, 8, 10, 14, 20, 50, 70, 80, 90, 100, 110, 125, 150, 170, 175, 176, 177, 180, 185, 190, or 200 amino acids long.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

As used herein, "substantially pure" means an object macromolecular species is the predominant macromolecular species present (i.e., on a molar basis it is more abundant than any other individual macromolecular species in the composition). In certain embodiments, a substantially purified fraction is a composition wherein the object macromolecular species comprises at least about 50 percent (on a weight basis) of all macromolecular species present. In certain embodiments, in a substantially pure composition, the object macromolecular species will comprise more than about 80%, 85%, 90%, 95%, or 99% by weight of all macromolecular species present in the composition. In certain embodiments, the object macromolecular species is purified to essentially homogeneity (i.e., contaminant species cannot be detected in the composition by conventional detection methods). In certain embodiments, the composition consists essentially of a single macromolecular species.

The term patient includes human and animal subjects.

Interleukin-1 receptor antagonist (IL-1ra) is a human protein that acts as an inhibitor of interleukin-1 activity and is a member of the IL-1 family, which also includes IL-1α and IL-1β. A non-exclusive, non-limiting, non-exhaustive list of IL-1 receptor antagonists includes Kineret® (anakinra) (e.g., a protein having the amino acid sequence of SEQ ID NO: 5), IL-1ra wild-type protein (including, but not limited to, a protein having the sequence of SEQ ID NO: 3 or a protein having the sequence of SEQ ID NO: 5), intracellular IL-1ra (icIL-1ra) (including, but not limited to, a protein having the sequence of SEQ ID NO: 6), IL-1ra β (see, e.g., PCT Publication No. WO 99/36541), IL-1ra variants, and IL-1ra derivatives. Certain IL-1ra receptor antagonists, including IL-1ra and variants and derivatives thereof, as well as methods of making and using them, are described, e.g., in U.S. Pat. Nos. 5,075,222; 6,599,873 B1; 5,863,769; 5,858,355; 5,739,282; 5,922,573; 6,054,559; WO 91/08285; WO 91/17184; WO 91/17249; AU 9173636; WO 92/16221; WO 93/21946; WO 94/06457; WO 94/21275; FR 2706772; WO 94/21235; DE 4219626, WO 94/20517; WO 96/22793; WO 96/12022; WO 97/28828; WO 99/36541; WO 99/51744. An IL-1 receptor antagonist may be glycosylated or non-glycosylated.

Exemplary IL-1ras include, but are not limited to, a polypeptide comprising an amino acid sequence as set forth in SEQ ID NO: 2 and fragments, variants, and derivatives of such a polypeptide that have an antagonist activity for the interleukin-1 receptor; a polypeptide comprising an amino acid sequence as set forth in SEQ ID NO: 3 and fragments, variants, and derivatives of such a polypeptide that have an antagonist activity for the interleukin-1 receptor; a polypeptide comprising an amino acid sequence as set forth in SEQ ID NO: 5 and fragments, variants, and derivatives of such a polypeptide that have an antagonist activity for the interleukin-1 receptor; and a polypeptide comprising an amino acid sequence as set forth in SEQ ID NO: 6 and fragments, variants, and derivatives of such a polypeptide that have an antagonist activity for the interleukin-1 receptor.

In certain embodiments, the term IL-1ra includes, but is not limited to, IL-1ra variants that have antagonist activity for the interleukin-1 receptor. In certain embodiments, IL-1ra variants are naturally occurring. In certain embodiments, IL-1ra variants are artificially constructed. Exemplary IL-1ra variants include, but are not limited to, amino acid sequences having one or more amino acid substitutions, deletions, and/or additions as compared to SEQ ID NO: 2, SEQ ID NO: 3, SEQ ID NO: 5, or SEQ ID NO: 6. In certain embodiments, IL-1ra variants comprise an amino acid sequence that is 95% identical to the amino acid sequence of SEQ ID NO: 3. In certain embodiments, IL-1ra variants comprise an amino acid sequence that is 90% identical to the amino acid sequence of SEQ ID NO: 3. In certain embodiments, IL-1ra variants comprise an amino acid sequence that is 85% identical to the amino acid sequence of SEQ ID NO: 3. In certain embodiments, IL-1ra variants comprise an amino acid sequence that is 75% identical to the amino acid sequence of SEQ ID NO: 3.

In certain embodiments, the term IL-1ra includes, but is not limited to, IL-1ra fragments that have antagonist activity for the interleukin-1 receptor. In certain embodiments, IL-1ra fragments are naturally occurring. In certain embodiments, IL-1ra fragments are artificially constructed. Exemplary IL-1ra fragments include, but are not limited to, fragments of the sequence set forth in SEQ ID NO: 2, SEQ ID NO: 3, SEQ ID NO: 5, or SEQ ID NO: 6. IL-1ra fragments are a subset of IL-1ra variants.

In certain embodiments, the term IL-1ra includes, but is not limited to, IL-1ra derivatives that have antagonist activity for the interleukin-1 receptor. In certain embodiments, IL-1ra derivatives are naturally occurring. In certain embodiments, IL-1ra derivatives are artificially constructed. Exemplary IL-1ra derivatives include, but are not limited to, chemically or enzymatically modified forms of the sequence set forth in SEQ ID NO: 2, SEQ ID NO: 3, SEQ ID NO: 5, or SEQ ID NO: 6. Exemplary IL-1ra derivatives also include, but are not limited to, chemically or enzymatically modified forms of variants of the sequence set forth in SEQ ID NO: 2, SEQ ID NO: 3, SEQ ID NO: 5, or SEQ ID NO: 6.

In certain embodiments, the term IL-1ra includes, but is not limited to, an IL-1ra having a secretory leader sequence. In certain embodiments, IL-1ra having a secretory leader sequence is referred to as "precursor IL-1ra." An exemplary precursor IL-1ra amino acid sequence is set forth in SEQ ID NO: 2. The term "precursor IL-1ra" includes fragments, variants, and derivatives of SEQ ID NO: 2 that are capable of being secreted and processed into a form having antagonist activity for the interleukin-1 receptor.

The term IL-1ra includes both aggregating IL-1ra and IL-1ra having reduced aggregation. Aggregating IL-1ra proteins have a lysine at position 93 and an arginine at position 97, but not all IL-1ra proteins with a lysine at position 93 and an arginine at position 97 are aggregating IL-1ras. "Aggregating IL-1ra" includes IL-1ra wild-type, variant, and derivative proteins that aggregate at 39° C. according to the following assay. A solution of 100 mg/ml of the subject IL-1ra is incubated at 39° C. in 10 mM phosphate, 140 mM NaCl, 0.5 mM EDTA, pH 6.5 (PSE). As a reference, a solution of 100 mg/ml of an IL-1ra wild-type protein having the sequence of SEQ ID NO: 5, is incubated in PSE at 39° C. The optical density of each solution is measured at 405 nm after 2 hours of incubation at 39° C. If the subject IL-1ra has an optical density after 2 hours of incubation that is at least 60% of the optical density of the IL-1ra wild-type protein after 2 hours of incubation, then the subject 1 L-1 ra is an aggregating 1 L-1 ra.

"IL-1ra having reduced aggregation" includes IL-1ra variant and derivative proteins that have an optical density that is less than 60% of the optical density of the IL-1ra wild-type protein in the assay described above.

In certain embodiments, the term "an IL-1ra that has antagonist activity for the interleukin-1 receptor" refers to an IL-1ra wild-type, variant, or derivative protein that is at least 50% as active as an IL-1ra wild-type protein having the amino acid sequence of SEQ ID NO: 5, in the IL-1ra signaling complex formation assay described in Example 3. "At least 50% as active" is determined by comparing the EC50 of the subject IL-1ra to the EC50 of IL-1ra wild-type protein.

The term "Arginine-97" refers to the amino acid residue at the 97th position in SEQ ID NO: 3 or the amino acid position in an IL-1ra that corresponds to the amino acid residue at the 97th position in SEQ ID NO: 3. For example, the amino acid that corresponds to arginine-97 of SEQ ID NO: 3 is the arginine at the 98th position of SEQ ID NO: 5. That arginine is still referred to as arginine-97 of IL-1ra. In certain embodiments, Arginine-97 is referred to as "R97," wherein the R is the single-letter code for arginine and 97 refers to its position in SEQ ID NO: 3. In certain embodiments, if R97 is replaced with another amino acid, the mutation may be referred to as R97X, wherein X is the single-letter code for the replacement amino acid. Thus, as a non-limiting example, if R97 is replaced by alanine, the mutation may be referred to as R97A.

The term "Lysine-93" refers to the amino acid residue at the 93rd position in SEQ ID NO: 3 or the amino acid position in an IL-1ra that corresponds to the amino acid residue at the 93rd position in SEQ ID NO: 3. For example, the amino acid that corresponds to lysine-93 of SEQ ID NO: 3 is the lysine at the 94th position of SEQ ID NO: 5. That lysine is still referred to as lysine-93 of IL-1ra. In certain embodiments, Lysine-93 is referred to as "K93," wherein the K is the single-letter code for lysine and 93 refers to its position in SEQ ID NO: 3. In certain embodiments, if K93 is replaced with another amino acid, the mutation may be referred to as K93X, wherein X is the single-letter code for the replacement amino acid. Thus, as a non-limiting example, if K93 is replaced by alanine, the mutation may be referred to as K93A.

The term "Tryptophan-16" refers to the amino acid residue at the 16th position in SEQ ID NO: 3 or the amino acid position in an IL-1ra that corresponds to the amino acid residue at the 16th position in SEQ ID NO: 3. For example, the amino acid that corresponds to tryptophan-16 of SEQ ID NO: 3 is the tryptophan at the 17th position of SEQ ID NO: 5. That tryptophan is still referred to as tryptophan-16 of IL-1ra. In certain embodiments, Tryptophan-16 is referred to as "W16," wherein the W is the single-letter code for tryptophan and 16 refers to its position in SEQ ID NO: 3. In certain embodiments, if W16 is replaced with another amino acid, the mutation may be referred to as W16X, wherein X is the single-letter code for the replacement amino acid. Thus, as a non-limiting example, if W16 is replaced by alanine, the mutation may be referred to as W16A.

The term "Tyrosine-34" refers to the amino acid residue at the 34th position in SEQ ID NO: 3 or the amino acid position in an IL-1ra that corresponds to the amino acid residue at the 34th position in SEQ ID NO: 3. For example, the amino acid that corresponds to tyrosine-34 of SEQ ID NO: 3 is the tyrosine at the 35th position of SEQ ID NO: 5. That tyrosine is still referred to as tyrosine-35 of IL-1ra. In certain embodiments, Tyrosine-34 is referred to as "Y34," wherein the Y is the single-letter code for tyrosine and 34 refers to its position in SEQ ID NO: 3. In certain embodiments, if Y34 is replaced with another amino acid, the mutation may be referred to as Y34X, wherein X is the single-letter code for the replacement amino acid. Thus, as a non-limiting example, if Y34 is replaced by alanine, the mutation may be referred to as Y34A.

In certain embodiments, "reduced aggregation" is defined as (1) aggregation of a polypeptide under condition A that is reduced relative to aggregation of the polypeptide under condition B; and/or (2) aggregation of a polypeptide variant under condition A that is reduced relative to aggregation of the wild-type polypeptide under the same condition A; and/or (3) aggregation of a polypeptide variant under condition A that is reduced relative to aggregation of a different polypeptide variant under the same condition A. As a non-limiting example, relative aggregation may be determined for case (1) as follows. The optical density at 405 nm of a polypeptide under condition A is measured at various times. The optical density at 405 nm of the polypeptide under condition B is then measured at the same various times. The aggregation curve for the object polypeptide under each condition is plotted with optical density on the y-axis and time on the x-axis. If the polypeptide under condition A has a lower optical density at time t than the polypeptide under condition B at the same time t, then the polypeptide under condition A is said to have reduced aggregation relative to the polypeptide under condition B.

Examples of different conditions include, but are not limited to, differences in buffer composition, differences in temperature, differences in polypeptide concentration, the presence and absence of accessory molecules, differences in accessory molecule concentration, etc.

The term "accessory molecule" refers to a molecule that reduces aggregation of one or more polypeptides. In certain embodiments, an accessory molecule reduces aggregation of one or more polypeptides nonspecifically. In certain embodiments, an accessory molecule reduces aggregation by interacting with one or more amino acids of the polypeptide. In certain embodiments, an accessory molecule interacts covalently with one or more amino acids of the polypeptide and is referred to as a "covalent accessory molecule." In certain embodiments, an accessory molecule interacts non-covalently with one or more amino acids of the polypeptide and is referred to as a "non-covalent accessory molecule."

In certain embodiments, the reduction in aggregation of a polypeptide is related to the concentration of the accessory molecule. In certain embodiments, an accessory molecule may substantially eliminate aggregation of a polypeptide. In certain embodiments, an accessory molecule reduces aggregation of a polypeptide by at least 10%. In certain embodiments, an accessory molecule reduces aggregation of a polypeptide by at least 20%. In certain embodiments, an accessory molecule reduces aggregation of a polypeptide by at least 30%. In certain embodiments, an accessory molecule reduces aggregation of a polypeptide by at least 40%. In certain embodiments, an accessory molecule reduces aggregation of a polypeptide by at least 50%. In certain embodiments, an accessory molecule reduces aggregation of a polypeptide by at least 60%. In certain embodiments, an accessory molecule reduces aggregation of a polypeptide by at least 70%. In certain embodiments, an accessory molecule reduces aggregation of a polypeptide by at least 75%. In certain embodiments, an accessory molecule reduces aggregation of a polypeptide by at least 80%. In certain embodiments, an accessory molecule reduces aggregation of a polypeptide by at least 85%. In certain embodiments, an accessory molecule reduces aggregation of a polypeptide by at least 90%. In certain embodiments, an accessory molecule reduces aggregation of a polypeptide by at least 95%.

In certain embodiments, an accessory molecule reduces the rate of aggregation of a polypeptide. In certain embodiments, the reduction in the rate of aggregation of a polypeptide is dependant on the concentration of the accessory molecule. In certain embodiments, an accessory molecule substantially eliminates aggregation of a polypeptide. In certain embodiments, an accessory molecule reduces the rate of aggregation of a polypeptide by at least 10%. In certain embodiments, an accessory molecule reduces the rate of aggregation of a polypeptide by at least 20%. In certain embodiments, an accessory molecule reduces the rate of aggregation of a polypeptide by at least 30%. In certain embodiments, an accessory molecule reduces the rate of aggregation of a polypeptide by at least 40%. In certain embodiments, an accessory molecule reduces the rate of aggregation of a polypeptide by at least 50%. In certain embodiments, an accessory molecule reduces the rate of aggregation of a polypeptide by at least 60%. In certain embodiments, an accessory molecule reduces the rate of aggregation of a polypeptide by at least 70%. In certain embodiments, an accessory molecule reduces the rate of aggregation of a polypeptide by at least 75%. In certain embodiments, an accessory molecule reduces the rate of aggregation of a polypeptide by at least 80%. In certain embodiments, an accessory molecule reduces the rate of aggregation of a polypeptide by at least 85%. In certain embodiments, an accessory molecule reduces the rate of aggregation of a polypeptide by at least 90%. In certain embodiments, an accessory molecule reduces the rate of aggregation of a polypeptide by at least 95%.

In certain embodiments, an accessory molecule interacts covalently or non-covalently with a polypeptide at one or more amino acid residues. In certain embodiments, an accessory molecule interacts with one or more specific amino acid residues. In certain embodiments, an accessory molecule does not substantially reduce the activity of the polypeptide. In certain embodiments, an accessory molecule does not reduce the activity of the polypeptide by more than 10%. In certain embodiments, accessory molecules to not reduce the activity of the polypeptide by more than 20%. In certain embodiments, an accessory molecule does not reduce the activity of the polypeptide by more than 30%. In certain embodiments, an accessory molecule does not reduce the activity of the polypeptide by more than 50%. In certain embodiments, an accessory molecule does not reduce the activity of the polypeptide by more than 75%.

In certain embodiments, an accessory molecule removes a charge present at an amino acid residue. In certain embodiments, an accessory molecule removes a charge by covalently modifying the amino acid residue. In certain embodiments, an accessory molecule removes a charge by non-covalently interacting with the amino acid residue, thereby "masking" the charge.

Exemplary covalent accessory molecules include, but are not limited to, 6-(N-(7-nitrobenz-2-oxa-1,3-diazol-4-yl)amino)hexanoic acid (NBD-X), methyl acetyl phosphate (MAP), and citraconic anhydride.

Exemplary non-covalent accessory molecules include, but are not limited to, sugars, single-charge anions, and multiple-charge anions. Exemplary sugars that may be accessory molecules include, but are not limited to, glycerol, sucrose, mannitol, and sorbitol. Exemplary single-charge anions that may be accessory molecules include, but are not limited to, phosphate and chloride. Exemplary multiple-charge anions that may be accessory molecules include, but are not limited to, pyrophosphate and citrate.

The term "arginine-reactive accessory molecule" refers to an accessory molecule that specifically interacts with arginine residues. In certain embodiments, an arginine-reactive accessory molecule interacts solely with arginine. In certain embodiments, an arginine-reactive accessory molecule interacts with arginine in addition to other amino acids. In certain embodiments, an arginine-reactive accessory molecule interacts covalently with arginine. In certain embodiments, an arginine-reactive accessory molecule interacts non-covalently with arginine. In certain embodiments, an arginine-reactive accessory molecule does not substantially reduce the activity of the polypeptide that contains the arginine.

The term "lysine-reactive accessory molecule" refers to an accessory molecule that specifically interacts with lysine residues. In certain embodiments, an lysine-reactive accessory molecule interacts solely with lysine. In certain embodiments, an lysine-reactive accessory molecule interacts with lysine in addition to other amino acids. In certain embodiments, an lysine-reactive accessory molecule interacts covalently with lysine. In certain embodiments, an lysine-reactive accessory molecule interacts non-covalently with lysine. In certain embodiments, an lysine-reactive accessory molecule does not substantially reduce the activity of the polypeptide that contains the lysine.

The term "multiple-charge anions" refers to molecules that comprise more than one negative charge at pH 6.5 and 25° C. In certain embodiments, multiple-charge anions have on average more than one, but less than two, negative charges at pH 6.5 and 25° C. In certain embodiments, multiple-charge anions have on average two or more negative charges at pH 6.5 and 25° C. In certain embodiments, multiple-charge anions have on average between two and four negative charges at pH 6.5 and 25° C. In various embodiments, one skilled in the art can determine whether a particular anion is a multiple-charge anion at pH 6.5 and 25° C., e.g., from the published pKa values for the anion. The term "single-charge anion" refers to an anion that has on average one, or less than one, negative charge at pH 6.5 and 25° C. In various embodiments, one skilled in the art can determine whether a particular anion is a single-charge anion at pH 6.5 and 25° C., e.g., from the published pKa values for the anion.

The term "sugar" refers to a carbohydrate. Exemplary sugars include, but are not limited to, monosaccharides, disaccharides, and trisaccharides. Non-limiting exemplary sugars include, but are not limited to, glycerol, sucrose, mannitol, and sorbitol.

A disease or medical condition is considered to be an "interleukin-1 mediated disease" if the spontaneous or experimental disease or medical condition is associated with elevated levels of IL-1 in bodily fluids or tissue and/or if cells or tissues taken from the body produce elevated levels of IL-1 in culture. In certain embodiments, such interleukin-1 mediated diseases are also recognized by one or more of the following two conditions: (1) pathological findings associated with the disease or medical condition can be mimicked experimentally in animals by administration of IL-1 or upregulation of expression of IL-1; and/or (2) a pathology induced in experimental animal models of the disease or medical condition can be inhibited or abolished by treatment with agents that inhibit the action of IL-1. In certain embodiments, one or more of the above conditions are met in an IL-1-mediated disease. In certain embodiments, all of the conditions are met in an IL-1-mediated disease.

Acute and chronic interleukin-1 (IL-1) mediated diseases include, but are not limited to, acute pancreatitis; amyotrophic lateral sclerosis (ALS, or Lou Gehrig's disease); Alzheimer's disease; cachexia/anorexia, including, but not limited to, AIDS-induced cachexia; asthma and other pulmonary diseases; atherosclerosis; autoimmune vasculitis; chronic fatigue syndrome; Clostridium associated illnesses, including, but not limited to, Clostridium-associated diarrhea; coronary conditions and indications, including, but not limited to, congestive heart failure, coronary restenosis, myocardial infarction, myocardial dysfunction (e.g., related to sepsis), and coronary artery bypass graft; cancer, including, but not limited to, leukemias, including, but not limited to, multiple myeloma leukemia and myelogenous (e.g., AML and CML), and tumor metastasis; diabetes (including, but not limited to, insulin-dependent diabetes); endometriosis; fever; fibromyalgia; glomerulonephritis; graft versus host disease and/or transplant rejection; hemohorragic shock; hyperalgesia; inflammatory bowel disease; inflammatory conditions of a joint, including, but not limited to, osteoarthritis, psoriatic arthritis, and rheumatoid arthritis; inflammatory eye disease, including, but not limited to, those associated with, for example, corneal transplant; ischemia, including, but not limited to, cerebral ischemia (including, but not limited to, brain injury as a result of, e.g., trauma, epilepsy, hemorrhage or stroke, each of which may lead to neurodegeneration); Kawasaki's disease; learning impairment; lung diseases (including, but not limited to, acute respiratory distress syndrome, or ARDS); multiple sclerosis; myopathies (e.g., muscle protein metabolism, including, but not limited to, muscle protein metabolism in sepsis); neurotoxicity (including, but not limited to, such condition induced by HIV); osteoporosis; pain, including, but not limited to, cancer-related pain; Parkinson's disease; periodontal disease; pre-term labor; psoriasis; reperfusion injury; septic shock; side effects from radiation therapy; temporal mandibular joint disease; sleep disturbance; uveitis; and inflammatory conditions resulting from, e.g., strain, sprain, cartilage damage, trauma, orthopedic surgery, infection, or other disease processes.

DETAILED DESCRIPTION OF CERTAIN EXEMPLARY EMBODIMENTS

Methods of reducing aggregation of an aggregating IL-1ra are provided. In certain embodiments, the aggregating IL-1ra whose aggregation is to be reduced comprises the amino acid sequence in SEQ ID NO: 2, SEQ ID NO: 3, SEQ ID NO: 5, or SEQ ID NO: 6. In certain embodiments, the aggregating IL-1ra whose aggregation is to be reduced comprises a fragment, variant, or derivative of a polypeptide having the amino acid sequence shown in SEQ ID NO: 2, SEQ ID NO: 3, SEQ ID NO: 5, or SEQ ID NO: 6, where that fragment, variant, or derivative has an antagonist activity for the interleukin-1 receptor.

Figure 8:
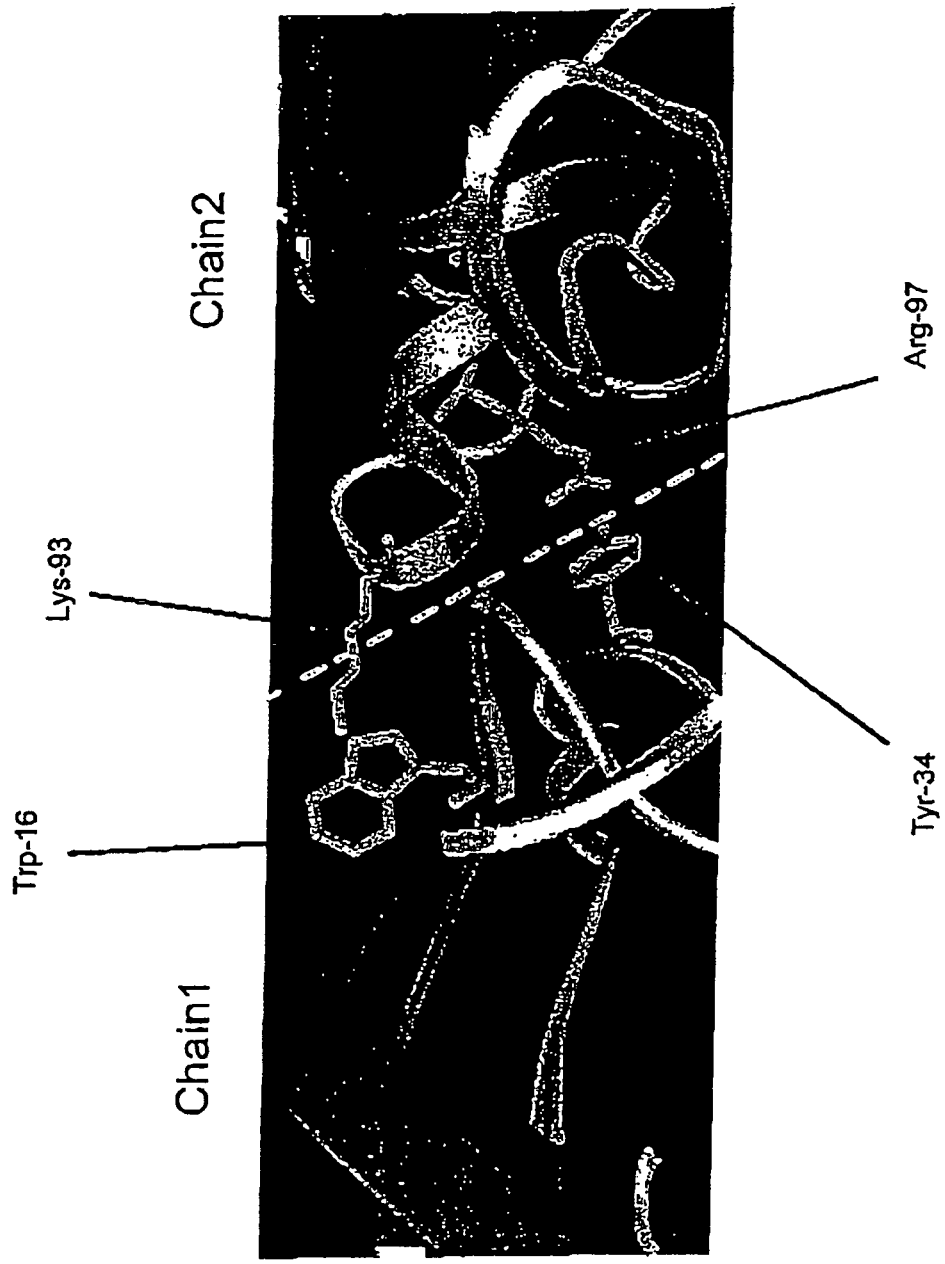
FIG. 8 shows a portion of the interface between the two subunits of the asymmetric IL-1ra dimer in the x-ray crystal structure described for FIG. 1.

Aggregation of IL-1ra may result from one or more cation-pi interactions between surface residues of two IL-1ra polypeptides. For example, as shown in FIG. 2, lysine-93 of one IL-1 polypeptide may form a cation-pi interaction with tryptophan-16 of a second IL-1 polypeptide. Similarly, arginine-97 of one polypeptide may form a cation-pi interaction with tyrosine-34 of a second polypeptide. Those interactions may cause two IL-1 ra polypeptides to bind to one another. Furthermore, because that binding is asymmetric, meaning that binding does not occur between the same face on both polypeptides, each polypeptide may be able to bind to two IL-1ra polypeptides simultaneously. In fact, if additional asymmetric binding contacts are possible between IL-1ra polypeptides, an IL-1ra polypeptide may be able to bind to more than two IL-1ra polypeptides simultaneously. If each IL-1ra polypeptide is capable of binding to at least two other IL-1ra polypeptides, e.g., through the asymmetric cation-pi interaction shown in FIG. 8, then those interactions may lead to aggregation of IL-1ra in solution.

In certain embodiments, aggregation of an aggregating IL-1ra may be reduced by reducing the positive charge at lysine-93, at arginine-97, or at both lysine-93 and arginine-97. In certain embodiments, if the positive charge at one or both of those positions is sufficiently reduced, the cation-pi interaction may not form, or may be weakened such that it is no longer stable enough to cause aggregation of IL-1ra. In certain embodiments, aggregation of an aggregating IL-1ra may be reduced by other mechanisms. The method is not limited by the mechanism of the reduction in aggregation. Any of the described methods of reducing aggregation may occur by the exemplary proposed mechanism discussed above or by any other mechanism that achieves the result described. Molecules that are capable of reducing aggregation of an aggregating IL-1ra are collectively referred to as "accessory molecules," regardless of their mechanism of reducing aggregation and regardless of whether they act covalently or non-covalently.

In certain embodiments, an accessory molecule may reduced aggregation of an aggregating IL-1ra by reducing the positive charge at one or both of lysine-93 or arginine-97. In various embodiments, an accessory molecule may reduce the positive charge at lysine-93, at arginine-97, or at both lysine-93 and arginine-97 covalently or non-covalently. An accessory molecule postulated to reduce the positive charge at one or both of those amino acids may also reduce aggregation through other mechanisms, or may act by other mechanisms entirely.

In certain embodiments, incubation of an aggregating IL-1ra with single-charge anionic or multiple-charge anionic molecules may reduce aggregation of IL-1ra. In certain embodiments, incubation of an IL-1ra having reduced aggregation with single-charge anionic or multiple-charge anionic molecules may further reduce aggregation of IL-1ra. In certain embodiments, that reduction in aggregation may result from the single-charge anionic or multiple-charge anionic molecule interacting with the positive charge at lysine-93, at arginine-97, or at both lysine-93 and arginine-97. As discussed in the work described in Example 2 and shown in FIG. 1, incubating an aggregating IL-1ra in CSE, which contains 10 mM citrate, reduced aggregation (as measured by the optical density at 405 nm) over time more than incubating the aggregating IL-1ra in PSE, which contains 10 mM phosphate. In that experiment, aggregation in CSE reached an $OD_{405}$ of about 0.55, while aggregation in PSE reached an $OD_{405}$ of about 1.2. Thus, incubation in CSE reduced aggregation by more than 50% relative to aggregation in PSE in that experiment.

Similarly, in the work described in Example 2, the rate of aggregation of aggregating IL-1ra in CSE was lower than the rate of aggregation of aggregating IL-1ra in PSE. The rate of aggregation in PSE in FIG. 1 is represented by the slope of the line marked as $K_{agg}$. A similar line may be drawn for CSE in FIG. 1, and that line would have a shallower slope, indicating a decreased rate of aggregation in CSE relative to PSE.

In certain embodiments, citrate may be more effective at reducing aggregation because it has a greater negative charge than phosphate at pH 6.5. In certain embodiments, certain amounts of negative charge may be more effective than others at reducing aggregation. Furthermore, in certain embodiments, certain configurations of negative charge, e.g., the distance between negative charges on an accessory molecule and how "fixed" those negative charges are in space, may also affect the effectiveness of accessory molecules. Thus, in certain embodiments, the effectiveness of various accessory molecules may be affected by the amount of negative charge, but the amount of negative charge may not always be determinative. In certain embodiments, a multiple-charge anion may be more effective at reducing aggregation than a single-charge anion. In various embodiments, one skilled in the art can select accessory molecules and determine which is appropriate for the specific application contemplated. For example, certain accessory molecules may be more or less effective at certain temperatures. In various embodiments, one skilled in the art can select an accessory molecule that is effective at the particular temperature at which the aggregating IL-1ra will be incubated or stored. In certain embodiments, an accessory molecule is selected that is effective at reducing aggregation between about 20° C. and 45° C. In certain embodiments, an accessory molecule is selected that is effective at reducing aggregation between about 25° C. and 45° C. In certain embodiments, an accessory molecule is selected that is effective at reducing aggregation between about 30° C. and 45° C. In certain embodiments, an accessory molecule is selected that is effective at reducing aggregation between about 35° C. and 45° C.

In certain embodiments, altering the concentration of an accessory molecule may affect the reduction in aggregation or the reduction in the rate of aggregation of an aggregating IL-1ra. The work discussed in Example 4 and shown in FIG. 3 considered the rate of aggregation of an aggregating IL-1ra incubated in various concentrations of phosphate, citrate, or pyrophosphate. In that experiment, citrate and pyrophosphate showed a similar correlation between a reduction in the rate of aggregation and the concentration of the accessory molecule. Both citrate and pyrophosphate showed an almost 90% reduction in the rate of aggregation at 10 mM accessory molecule. That reduction increased for both citrate and pyrophosphate at 20 mM, and then leveled off up to over 100 mM. In contrast, phosphate showed only about a 20% reduction in the rate of aggregation at 10 mM, and the reduction didn't level off until about 80 mM. The results of the experiment discussed in Example 4 suggest that pyrophosphate and citrate are substantially equally effective at reducing the rate of aggregation of an aggregating IL-1ra at 29° C. Both citrate and pyrophosphate have a greater negative charge than phosphate at pH 6.5, suggesting that, in certain embodiments, the amount of negative charge may affect the efficiency of certain accessory molecules.

In certain embodiments, a sugar may be an accessory molecule. Exemplary sugars that may be accessory molecules include, but are not limited to, sucrose, glycerol, mannitol, and sorbitol. Example 5 describes an exemplary experiment in which increasing concentrations of sucrose, glycerol, or sorbitol reduced the rate of aggregation of an aggregating IL-1ra (see FIG. 4). At 3%, each of the three sugars reduced the rate of aggregation to less than 5 aggregation units (a.u.; 1 a.u. is equal to an increase of 1 milli-optical density unit at 405 nm per minute using a volume of 200 µl and a SpectroMax™ plate-reading spectrophotometer), compared to a rate of aggregation of greater than 20 a.u. at 0% sugar.

In various embodiments, one skilled in the art can determine the appropriate concentration of a non-covalent accessory molecule for a particular application by using, e.g., the methods of Example 4 or Example 5. In certain embodiments, an accessory molecule may be present at a concentration of 1 to 100 mM. In certain embodiments, an accessory molecule may be present at a concentration of 1 to 50 mM. In certain embodiments, an accessory molecule may be present at a concentration of 1 to 20 mM. In certain embodiments, an accessory molecule may be present at a concentration of 10 mM.

In certain embodiments, an accessory molecule may be present at a concentration of between 0 and 10%. In certain embodiments, an accessory molecule may be present at a concentration of between 0 and 5%. In certain embodiments, an accessory molecule may be present at a concentration of 1%, 2%, or 3%.

In certain embodiments, the $K_d$ of a non-covalent accessory molecule for IL-1ra is less than 10 mM. In certain embodiments, the $K_d$ of a non-covalent accessory molecule for IL-1ra is less than 7 mM. In certain embodiments, the $K_d$ of a non-covalent accessory molecule for IL-1ra is less than 5 mM. In certain embodiments, the $K_d$ of a non-covalent accessory molecule for IL-1ra is less than 4 mM. In certain embodiments, the $K_d$ of a non-covalent accessory molecule for IL-1ra is less than 3 mM. In certain embodiments, the $K_d$ of a non-covalent accessory molecule for IL-1ra is between 0.1 mM and 5 mM. In certain embodiments, the $K_d$ of a non-covalent accessory molecule for IL-1ra is between 1 mM and 5 mM. In certain embodiments, the $K_d$ of a non-covalent accessory molecule for IL-1ra is between 0.1 mM and 4 mM. In certain embodiments, the $K_d$ of a non-covalent accessory molecule for IL-1ra is between 1 mM and 4 mM. In certain embodiments, the $K_d$ of a non-covalent accessory molecule for IL-1ra is between 2 mM and 4 mM.

In certain embodiments, an accessory molecule may reduce aggregation by covalently modifying an aggregating IL-1ra. In certain embodiments, an accessory molecule may further reduce aggregation by covalently modifying an IL-1ra having reduced aggregation. In certain embodiments, the covalent modification removes a positive charge at lysine-93, at arginine-97, or at both lysine-93 and arginine-97. In certain embodiments, a covalent accessory molecule may reduce aggregation by another mechanism, e.g., by sterically inhibiting formation of one or more cation-pi interactions or other interactions between aggregating IL-1ra polypeptides.

Non-limiting exemplary accessory molecules that may covalently modify an IL-1ra include, but are not limited to, NBD-X, MAP, and citraconic anhydride. In certain embodiments, NBD-X forms a derivative with primary amines. In the work discussed in Example 3 and shown in FIG. 2, incubation of IL-1ra wild-type protein with NBD-X, SE resulted in derivatization of the amino-terminal amine group of the polypeptide and of lysine-93. In certain embodiments, derivatization with NBD-X may remove the positive charge at lysine-93 and may result in reduced aggregation of derivatized IL-1 ra. In certain embodiments, MAP acetylates lysine residues and the N-terminal amino groups of polypeptides. In the work discussed in Example 7 and shown in FIGS. 13-15, incubation of IL-1ra with MAP at various times of incubation, resulted in derivatization of the N-terminal amino group of IL-1ra; derivatization of the N-terminal amino group and lysine-6 of IL-1ra; derivatization of the N-terminal amino group, lysine-6, and lysine-93 of IL-1ra; or derivatization of the N-terminal amino group, lysine-6, lysine-93, and lysine-96 of IL-1ra. In certain embodiments, derivatization with MAP may remove the positive charge at lysine-93 and may result in reduced aggregation of derivatized IL-1ra.

In certain embodiments, other amine-reactive molecules may reduce aggregation of an aggregating IL-1ra by removing one or more positive charges or through another mechanism. In certain embodiments, IL-1 ra that has been derivatized with a covalent accessory molecules is at least 90% as active as an IL-1ra wild-type protein that has not been similarly derivatized. In certain embodiments, IL-1ra that has been derivatized with a covalent accessory molecules is at least 80% as active as an IL-1ra wild-type protein that has not been similarly derivatized. In certain embodiments, IL-1ra that has been derivatized with a covalent accessory molecules is at least 75% as active as an IL-1ra wild-type protein that has not been similarly derivatized. In certain embodiments, IL-1ra that has been derivatized with a covalent accessory molecules is at least 50% as active as an IL-1ra wild-type protein that has not been similarly derivatized.

In certain embodiments, kits comprising IL-1ra and at least one accessory molecule are provided. Kits may optionally include instructions for combining the IL-1ra and the at least one accessory molecule, if the components are provided separately. In certain embodiments, kits include instructions for using the IL-1ra and the at least one accessory molecule. In certain embodiments, the kits may comprise at least one covalent accessory molecule and/or at least one non-covalent accessory molecule. When the kit comprises at least one covalent accessory molecule, the kit may further comprise instructions for removing any remaining unreacted accessory molecule from the derivatized IL-1ra following incubation of IL-0.1ra with the covalent accessory molecule. In certain embodiments, kits contain IL-1ra that has already been derivatized with at least one covalent accessory molecule. Similarly, in certain embodiments, a kit may contain an IL-1ra that is already in a composition with at least one non-covalent accessory molecule.

In certain embodiments, pharmaceutical compositions are provided comprising a therapeutically effective amount of IL-1ra together with a pharmaceutically acceptable diluent, carrier, solubilizer, emulsifier, preservative and/or adjuvant.

In certain embodiments, acceptable formulation materials are nontoxic to recipients at the dosages and concentrations employed.

In certain embodiments, a pharmaceutical composition may comprise formulation materials for modifying, maintaining and/or preserving, for example, the pH, osmolarity, viscosity, clarity, color, isotonicity, odor, sterility, stability, rate of dissolution or release, adsorption, and/or penetration of the composition. Exemplary formulation materials include, but are not limited to, amino acids (such as glycine, glutamine, asparagine, arginine, and lysine); antimicrobials; antioxidants (such as ascorbic acid, sodium sulfite, and sodium hydrogen-sulfite); buffers (such as borate, bicarbonate, Tris-HCl, citrates, phosphates, and other organic acids); bulking agents (such as mannitol and glycine); chelating agents (such as ethylenediamine tetraacetic acid (EDTA)); complexing agents (such as caffeine, polyvinylpyrrolidone, beta-cyclodextrin, and hydroxypropyl-beta-cyclodextrin); fillers; monosaccharides; disaccharides; and other carbohydrates (such as glucose, mannose, and dextrins); proteins (such as serum albumin, gelatin, and immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid, and hydrogen peroxide); solvents (such as glycerin, propylene glycol, and polyethylene glycol); sugar alcohols (such as mannitol and sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose and sorbitol); tonicity enhancing agents (such as alkali metal halides, such as sodium and potassium chloride, mannitol, sorbitol); delivery vehicles; diluents; excipients and pharmaceutical adjuvants. (See, e.g., Remington's Pharmaceutical Sciences, 18th Edition, A. R. Gennaro, ed., Mack Publishing Company (1990).

In certain embodiments, an IL-1ra and/or one or more additional therapeutic agent are linked to a half-life extending vehicle. Exemplary vehicles include, but are not limited to, the Fc domain, polyethylene glycol, and dextran. Certain exemplary vehicles are described, e.g., in U.S. application Ser. No. 09/428,082 and published PCT Application No. WO 99/25044.

In certain embodiments, an optimal pharmaceutical composition will be determined by one skilled in the art depending upon, for example, the intended route of administration, delivery format, and desired dosage. See, for example, Remington's Pharmaceutical Sciences, supra. In certain embodiments, such compositions may influence the physical state, stability, rate of in vivo release, and rate of in vivo clearance of the IL-1ra.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a composition comprising an IL-1ra, with or without at least one accessory molecule and/or one or more additional therapeutic agents, may be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an IL-1ra, with or without at least one accessory molecule and/or one or more additional therapeutic agents, may be formulated as a lyophilizate using appropriate excipients such as sucrose.

In certain embodiments, the pharmaceutical compositions of the invention can be selected for parenteral delivery. In certain embodiments, the compositions may be selected for inhalation or for delivery through the digestive tract, such as orally. The preparation of such pharmaceutically acceptable compositions is within the skill of the art.

In certain embodiments, when parenteral administration is contemplated, a therapeutic composition may be in the form of a pyrogen-free, parenterally acceptable aqueous solution comprising the desired IL-1ra, with or without at least one accessory molecule and/or one or more additional therapeutic agents, in a pharmaceutically acceptable vehicle. In certain embodiments, a vehicle for parenteral injection is sterile distilled water in which the IL-1ra, with or without at least one accessory molecule and/or one or more additional therapeutic agents, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, an IL-1ra, with or without at least one accessory molecule and/or one or more additional therapeutic agents, may be formulated as a dry powder for inhalation. In certain embodiments, an inhalation solution comprising an IL-1ra, with or without at least one accessory molecule and/or one or more additional therapeutic agents, may be formulated with a propellant for aerosol delivery. In certain embodiments, solutions may be nebulized. Pulmonary administration is further described in PCT application no. PCT/US94/001875, which describes pulmonary delivery of chemically modified proteins.

In certain embodiments, it is contemplated that formulations may be administered orally. In certain embodiments, an IL-1ra, with or without at least one accessory molecule and/or one or more additional therapeutic agents, that is administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of the IL-1ra and/or any accessory molecules and/or any additional therapeutic agents. In certain embodiments, diluents, flavorings, low melting point waxes, vegetable oils, lubricants, suspending agents, tablet disintegrating agents, and binders may also be employed.

In certain embodiments, a pharmaceutical composition may involve an effective quantity of IL-1ra, with or without at least one accessory molecule and/or one or more additional therapeutic agents, in a mixture with non-toxic excipients which are suitable for the manufacture of tablets. In certain embodiments, by dissolving the tablets in sterile water, or another appropriate vehicle, solutions may be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving IL-1ra, with or without at least one accessory molecule and/or one or more additional therapeutic agents, in sustained- or controlled-delivery formulations. In certain embodiments, techniques for formulating a variety of other sustained- or controlled-delivery products, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (see, e.g., U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions may include liposomes, which can be prepared by any of several methods known in the art. See e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, after the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, kits are provided for producing a single-dose administration unit. In certain embodiments, the kits may each contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an IL-1ra, with or without at least one accessory molecule and/or one or more additional therapeutic agents, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the IL-1ra, with or without at least one accessory molecule and/or one or more additional therapeutic agents, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of the IL-1ra and/or any accessory molecules and/or any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising an IL-1ra, with or without at least one accessory molecule and/or one or more additional therapeutic agents, in an ex vivo manner. In such instances, cells, tissues and/or organs that have been removed from the patient are exposed to a pharmaceutical composition comprising an IL-1ra, with or without at least one accessory molecule and/or one or more additional therapeutic agents, after which the cells, tissues and/or organs are subsequently implanted back into the patient.

In certain embodiments, an IL-1ra having reduced aggregation and/or any accessory molecules and/or any additional therapeutic agents can be delivered by implanting certain cells that have been genetically engineered, using methods known in the art, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the present invention.

Example 1

Production of IL-1ra Wild-Type Protein

Human recombinant interleukin-1 receptor antagonist (IL-1ra) having the sequence of SEQ ID NO: 5, can be prepared at Amgen manufacturing facilities according to the method discussed in European Patent No. EP 0 502 956 B1, in which the cell recovery step is optional. Alternatively, anakinra, which has the amino acid sequence of SEQ ID NO: 5, may be obtained from Amgen Inc., Thousand Oaks, Calif. Purified human IL-1 ra having the amino acid sequence of SEQ ID NO: 5 was used in the examples described herein.

Example 2

IL-1ra Aggregation

IL-1ra aggregation in phosphate buffer and citrate buffer at 39° C. was determined as follows. Ten ml of an IL-1ra stock solution (200-220 mg/ml protein in 10 mM sodium citrate, 140 mM NaCl, 0.5 mM EDTA, pH 6.5 (CSE)) was dialyzed overnight at 4° C. against either 2×2L of 10 mM phosphate, 140 mM NaCl, 0.5 mM EDTA, pH 6.5 (PSE) or 2×2L of CSE. The dialyzed solution was filtered through a 0.2 μm filter and the IL-1ra protein concentration was adjusted to 140 mg/ml by diluting with the appropriate buffer.

Aggregation of IL-1ra in each buffer was measured using a 96-well glass plate (Zissner) and a temperature-controlled plate reading spectrophotometer, SpectraMax Plus (Molecular Devices). The sample size per well was 180 μlμl. The plates were incubated in the spectrophotometer at 39° C. and the optical density measured at 405 nm every 1 minute. FIG. 1 shows the optical density at 405 nm plotted as a function of time for this experiment. The rate of aggregation was determined as the slope of the initial linear region of the saturation curve using the SoftMax Pro program (Molecular Devices). The rate of aggregation of IL-1ra incubated in CSE is reduced relative to the rate of aggregation of IL-1ra incubated in PSE. Furthermore, the extent of aggregation of IL-1ra incubated in CSE is reduced relative to the extent of aggregation of IL-1ra incubated in PSE.

Example 3

NBD-X Labeling of IL-1ra

Surface-exposed amino groups were identified by labeling IL-1ra with NBD-X, SE (succinimidyl 6-(N-(7-nitrobenz-2-oxa-1,3-diazol-4yl)amino)hexanoate, Molecular Probes). NBD-X becomes fluorescent upon derivitization with amino groups. Twenty μlμl of 0.2 mM IL-1ra in PSE was diluted with 480 μlμl PSE. Eight μl of 50 μg/μlμl NBD-X, SE solution in dimethyl formamide was added to the IL-1ra solution in 2 μlμl increments at room temperature. The reaction was incubated for one hour at room temperature, then stopped by the addition of 50 μlμl of a 1.5 M hydroxylamine solution, pH 8.5. The reaction mixture was passed through a desalting gel filtration column that was pre-equilibrated with PSE. The protein peak was collected and further analyzed by RP-HPLC and LC-MS/MS as follows.

Reverse-phase HPLC was conducted using a Phenomenex Jupiter™ 5μ, C4 column (300 Å, 250×4.6 mm) and an HP1100 HPLC system equipped with on-line absorbance and fluorescence detectors. The absorbance was measured at 215 nm to detect the presence of the polypeptide. Fluorescent emission was measured at 535 nm following excitation at 480 nm to detect the presence of the amine-derivatized NBD-X. The elution was performed with a linear 30-45% gradient of methanol in 0.1% trifluoroacetic acid (TFA) and water (v/v/v). FIG. 2 shows the absorbance of NBD-X labeled IL-1ra at 215 nm and the fluorescent emission of NBD-X labeled IL-1ra at 535 nm following excitation at 480 nm for this experiment. The identity of the fluorescing peaks was determined as follows.

Two major fluorescing peaks were identified, an early-eluting peak at 16.75 minutes and a later-eluting peak at 17.5 minutes. See FIG. 2, lower panel. The peaks were collected manually and digested with Lys-C endoproteinase as follows. Each peak was collected from five separate HPLC runs. All of the fractions primarily containing the 16.75 peak were pooled together. All of the fractions primarily containing the 17.5 minute peak were pooled together. The two pooled samples were then dried with centrifugation using a SpeedVac concentrator. Each of the pooled samples was then dissolved in 490 μlμl of digestion buffer, which contained 10 mM Tris, 0.8 M guinidinium hydrochloride, pH 8.0. Ten μl of a Lys-C proteinase solution, prepared by dissolving 5 μg Lys-C proteinase (sequencing grade, Roche Diagnostics) in 50 μl digestion buffer, was then added to each pooled sample. The samples were digested overnight at 37° C. Following digestion, the peptides generated were subjected to LC-MS/MS using a Finnegan LCQ Deca equipped with a Beckman System Gold HPLC according to the standard manufacturer's protocol.

For the early-eluting peak (16.75 min), digestion yielded a unique peptide of mass 1107.8 m/z, corresponding to an amino-terminal peptide of IL-1ra with an added mass of 276 amu, which suggests the presence of an NBD derivative. MS/MS analysis of the peptide produced fragments consistent with the amino acid sequence MRPSGRK plus an extra mass of 276 amu on the methionine residue, suggesting that the amino-terminal methionine of IL-1ra was derivatized with NBD-X.

Digestion of the later-eluting peak (17.5 min) yielded a unique peptide of mass 1145.9 m/z, which suggested an IL-1ra peptide corresponding to residues 72-96 comprising an NBD derivative. MS/MS analysis of the peptide produced fragments consistent with the amino acid sequence corresponding to residues 72-96 with an NBD-derivatized lysine at position 93.

According to the foregoing results, the lysine at position 93 of IL-1 ra is capable of derivatization with NBD-X under the conditions used in this experiment. These results also suggest that the lysine at position 93 is exposed and is a solvent-accessible residue in the intact IL-1ra protein.

Example 4

Rate of Aggregation of IL-1ra in the Presence of Phosphate, Citrate, or Pyrophosphate The rate of aggregation of IL-1ra was determined in several different buffer compositions. Ten ml of an IL-1ra stock solution (220 mg/ml in CSE) was dialyzed against 2×4L of 140 mM NaCl using Pierce Snakeskin dialysis tubing (3.5 kDa cut-off) at 4° C. Aliquots of the dialyzed IL-1ra solution were brought to various concentrations of citrate, phosphate, or pyrophosphate by addition of 0.45M citrate, 0.5M phosphate, or 0.45M pyrophosphate stock solutions (all pH 6.5) and an appropriate volume of 140 mM NaCl to result in a final concentration of IL-1ra in each sample of 140 mg/ml. The final concentration of citrate, phosphate, or pyrophosphate in each sample ranged from 1 to 125 mM.

Figure 3:
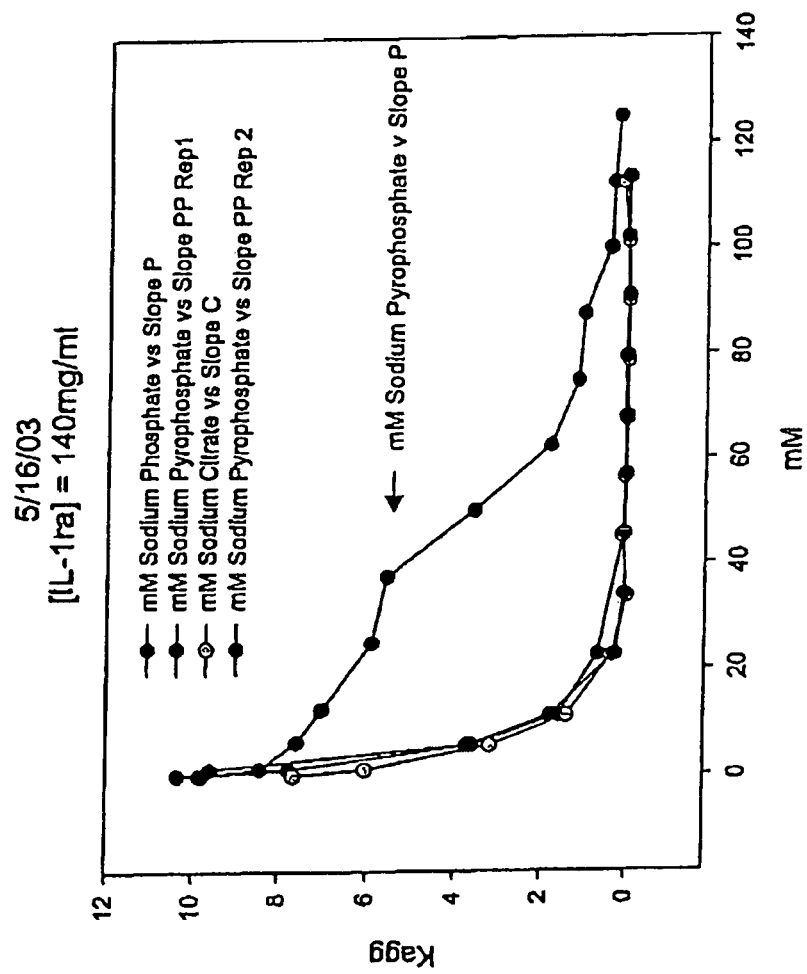
FIG. 3 shows the rates of aggregation for IL-1ra wild-type protein in the presence of increasing concentrations of phosphate, pyrophosphate, and citrate anions discussed in Example 4.

Aggregation of IL-1ra in each sample was monitored for 4 hours at 29° C. by measuring the light scattering at 405 nm at one minute intervals as described in Example 2 above. The rate of aggregation was determined as the slope of the linear region of the saturation curve calculated using the SoftMax Pro program (Molecular Devices). FIG. 3 shows that in this experiment, the rate of aggregation of IL-1ra decreased with increasing concentrations of citrate, phosphate, or pyrophosphate. Notably, the rate of aggregation of IL-1ra in citrate or pyrophosphate buffer decreased more rapidly than the rate of aggregation in phosphate buffer.

The estimated pKa's of the three ionizable hydrogens on phosphate are 2.148, 7.198, and 12.35 at pH 6.5 and 39° C. The estimated pKa's of the three ionizable hydrogens on citrate are 3.128, 4.761, and 6.396 at pH 6.5 and 39° C. The estimated pKa's of the four ionizable hydrogens on pyrophosphate are 0.83, 2.26, 6.72, and 9.46 at pH 6.5 and 39° C. See, e.g., Goldberg et al., Thermodynamic quantities for the ionization reactions of buffers. *J. Phys. Chem. Ref. Data,* 31(2): 231-370 (2002). Accordingly, phosphate is predicted to have predominantly one negative charge at pH 6.5 and 39° C., while citrate is predicted to have three negative charges at pH 6.5 and 39° C. and pyrophosphate is predicted to have between two and three negative charges at pH 6.5 and 39° C., as estimated according to the literature-reported pKas discussed above.

Thus, these results suggest that multiple-charge anions may reduce the rate of aggregation of IL-1ra more effectively than single-charge anions at a particular pH. Consistent with that conclusion, NaCl, which is a single-charge anion, was found to have a similar aggregation rate profile as phosphate (data not shown).

Example 5

Figure 4:
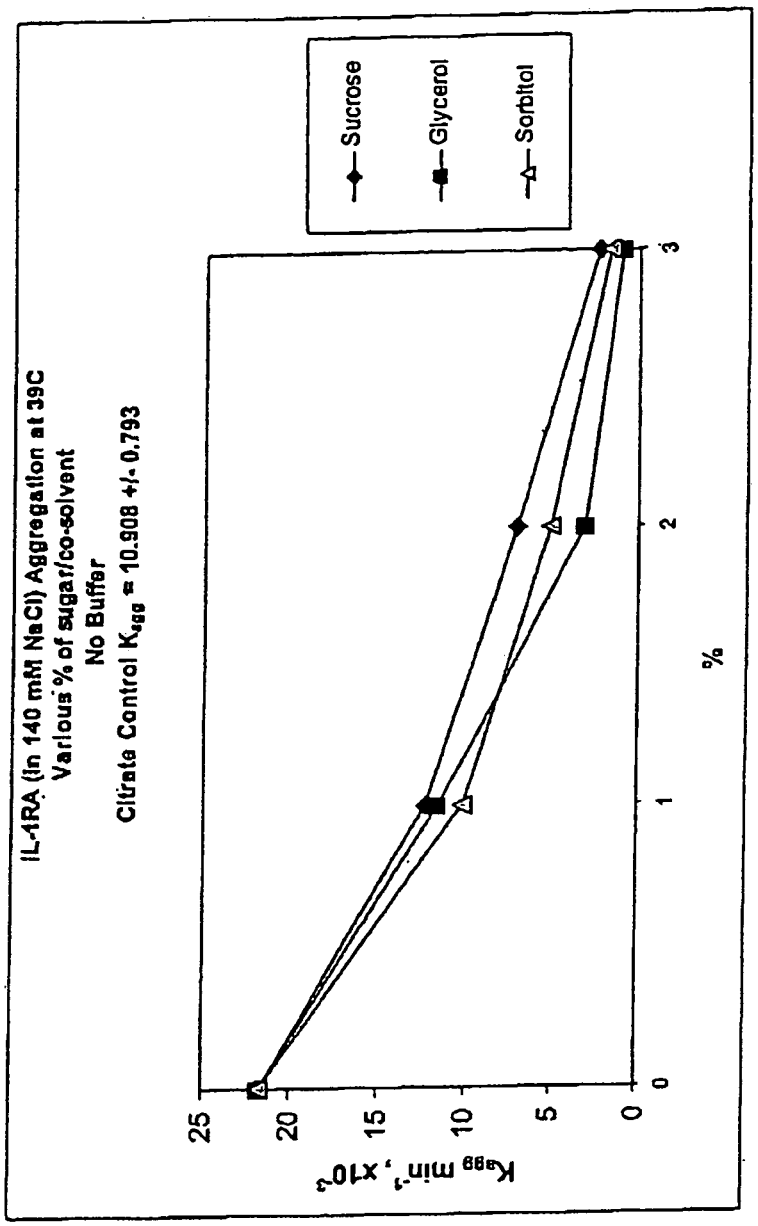
FIG. 4 shows the aggregation rates for IL-1ra wild-type protein in the presence of increasing concentrations of glycerol, sorbitol, or sucrose discussed in Example 5.
Figure 7:
FIG. 7 shows an exemplary x-ray crystal structure of IL-1ra.

Rate of Aggregation of IL-1 ra in the Presence of Sucrose, Glycerol, or Sorbitol The rate of aggregation of IL-1ra was determined in the presence of several different sugars. Ten ml of an IL-1ra stock solution (220 mg/ml in CSE) was dialyzed against 2×4 L of 140 mM NaCl using Pierce. Snakeskin dialysis tubing (3.5 kDa cut-off) at 4° C. Aliquots of the dialyzed IL-1 ra solution were brought to various percent concentrations of sucrose, glycerol, or sorbitol by addition of 25% sucrose, 25% glycerol, or 25% sorbitol stock solutions and an appropriate volume of 140 mM NaCl to result in a final concentration of IL-1ra in each sample of 140 mg/ml. The final concentration of sucrose, glycerol, or sorbitol in each sample was 0%, 1%, 2%, or 3%. The rate of aggregation was determined by measuring the optical density of each IL-1ra solution at 39° C. using the method described in Example 2. FIG. 4 shows that in this experiment, increasing concentrations of sugar resulted in decreasing rates of aggregation of IL-1ra. At 0% sugar, the rate of aggregation of IL-1ra in this experiment was about 22 aggregation units (a.u., measured as the increase in milli-optical density at 405 nm per minute). At 3% sucrose, glycerol, or sorbitol, the rate of aggregation of IL-1ra was reduced to between 0 and 5 a.u.

Example 6

Urea- and Guanidinium Hydrochloride-Induced Unfolding of IL-1ra

Figure 9:
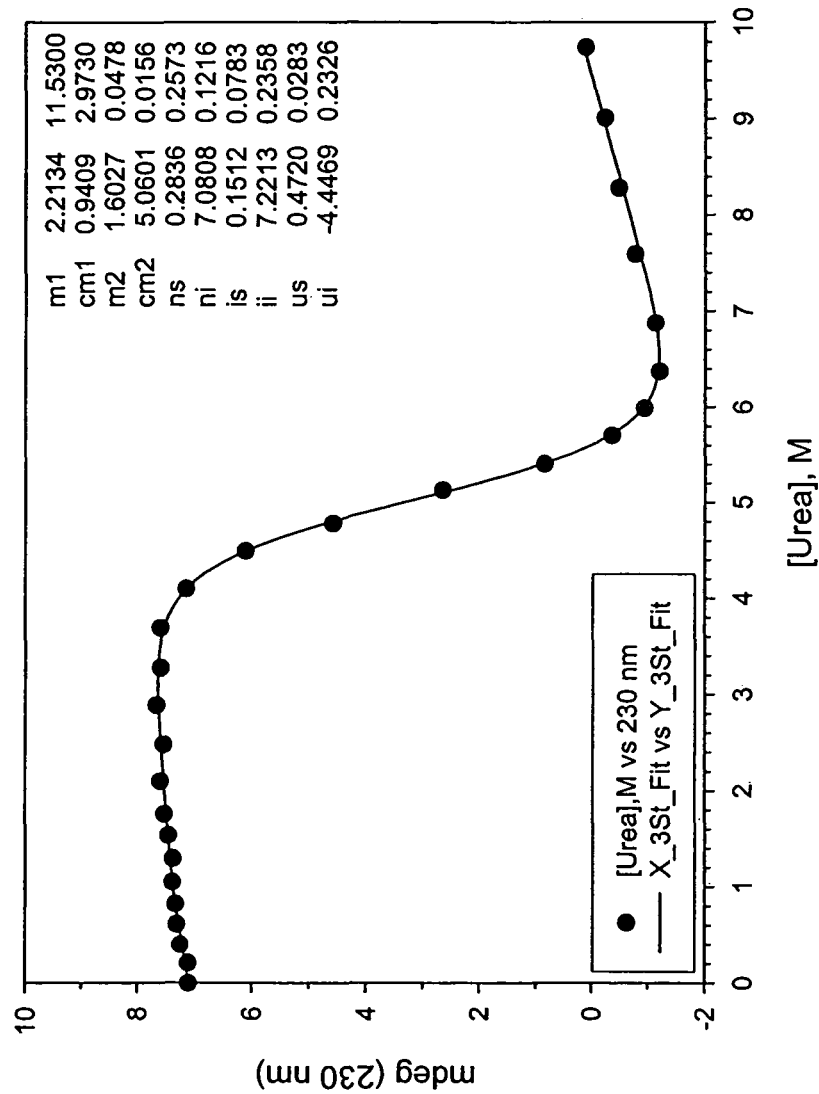
FIG. 9 shows the urea-induced equilibrium unfolding of IL-1ra detected by circular dichroism discussed in Example 6.

Equilibrium urea-induced unfolding of IL-1ra was performed as follows. For far-UV circular dichroism studies, 1-1.5 ml samples of 0.86 mg/ml IL-1ra and various concentrations of urea (between about 0 and 10M) were wrapped in foil to protect them from light and incubated overnight (>12 hours) at room temperature. The circular dichroism at 230 nm was then determined for each sample at 23° C. FIG. 9 shows the circular dichroism signal at 230 nm for IL-1ra incubated in various concentrations of urea for this experiment. The data were plotted and the unfolding curve was fitted to a 3-state model, native state <-> intermediate state <-> unfolded state. In this model, ml, which is the slope of the first transition, and $C_{m1}$, which is the midpoint of the first transition were constrained. Those parameters were constrained because far-UV CD cannot distinguish between the native and the intermediate states. The constrained values for m1 and $C_{m1}$ were obtained by averaging the values from several fluorescence measurements, which were able to distinguish the native state from the intermediate state. As shown in FIG. 9, IL-1ra underwent a global unfolding transition between about 4 and 6 M urea in this experiment.

Figure 10:
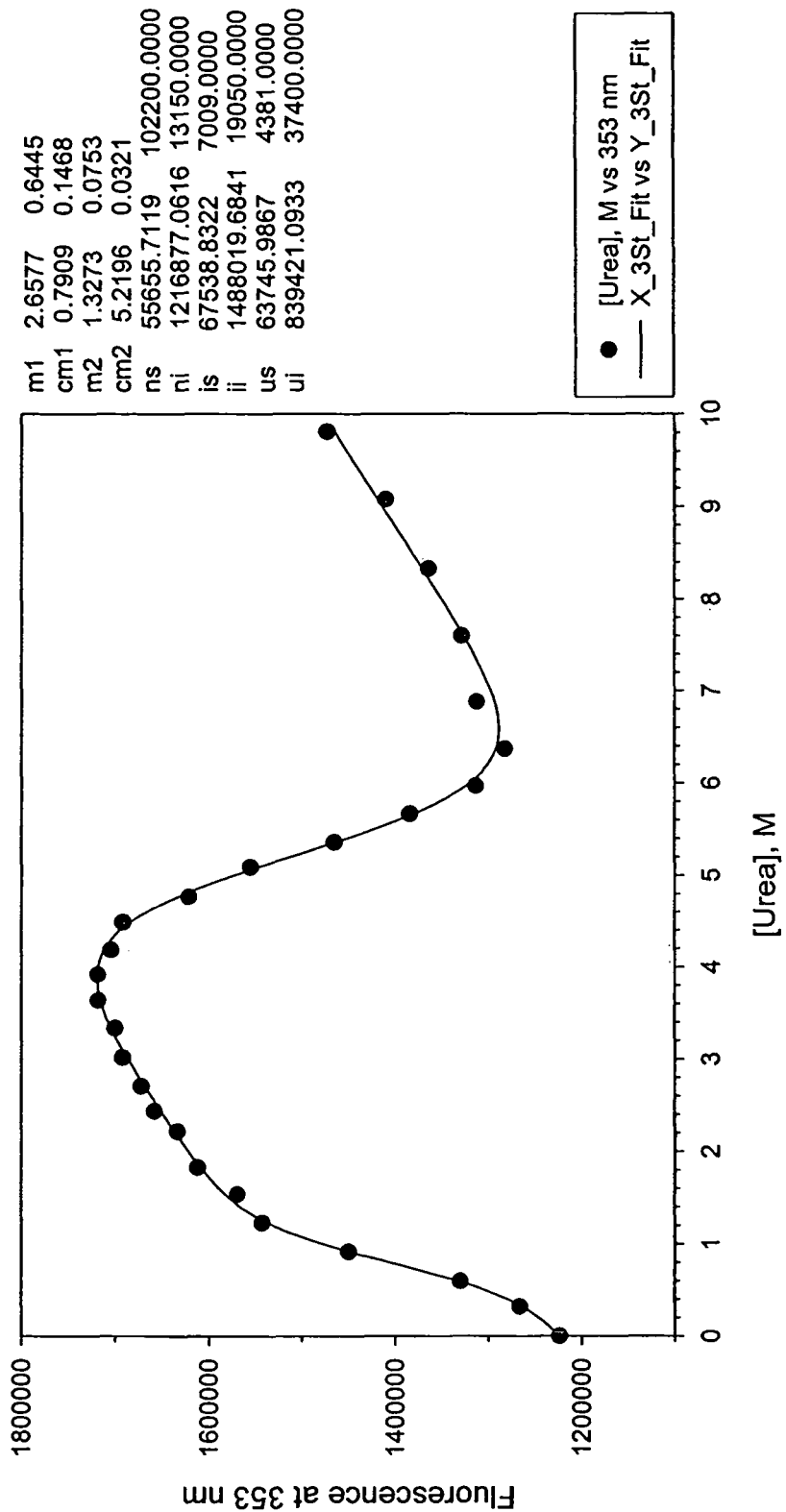
FIG. 10 shows the urea-induced equilibrium unfolding of IL-1ra detected by intrinsic fluorescence discussed in Example 6.

For fluorescence studies, 1-1.5 ml samples of 0.086 mg/ml IL-1ra and various concentrations of urea (between about 0 and 10M) were wrapped in foil to protect them from light and incubated overnight (>12 hours) at room temperature. FIG. 10 shows the intrinsic fluorescence at 353 nm of IL-1ra incubated in various concentrations of urea. The data were plotted and the unfolding curve was fitted to the 3-state model discussed above. No constraints were applied in this experiment. As shown in FIG. 10, the fluorescence experiment suggests the presence of an unfolding transition between 0 and about 1.5 M urea. Since that transition is not observed in the far-UV CD experiment, it may reflect accumulation of an intermediate state with a native-like secondary structure. That intermediate state may involve more local changes to the structure, e.g., destabilization of surface loops, while the hydrophobic core of IL-1ra may remain substantially unperturbed.

Figure 11:
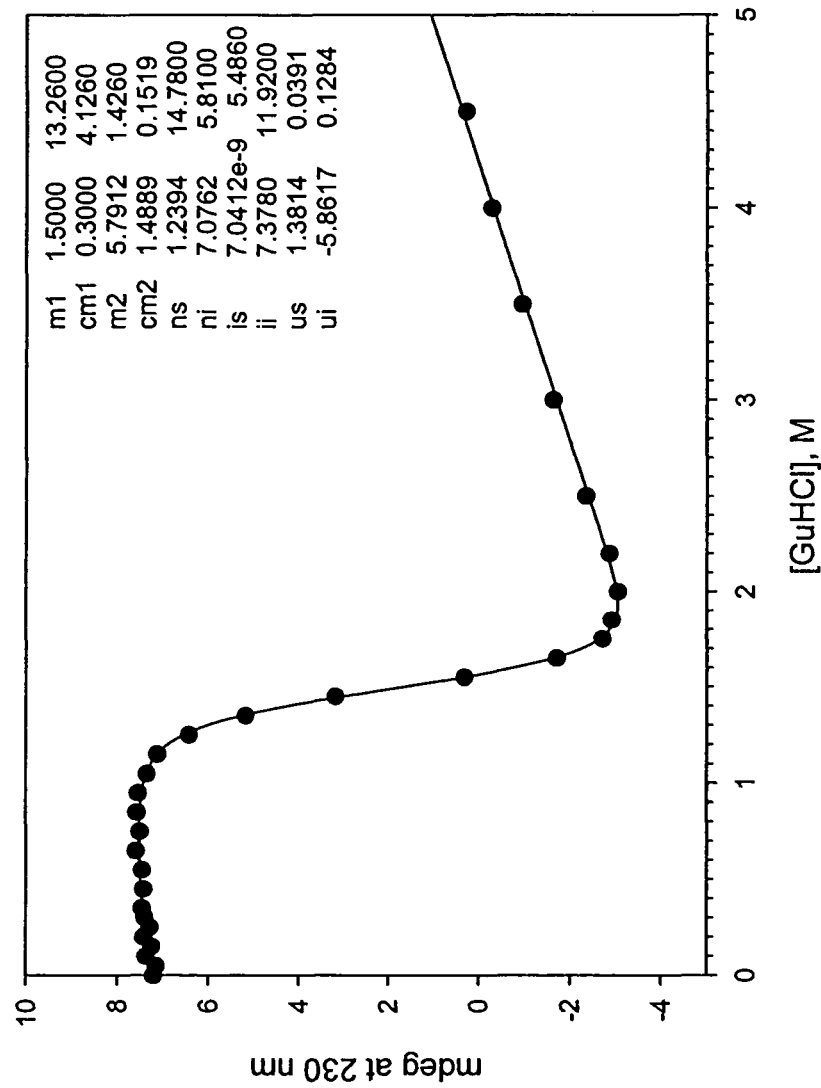
FIG. 11 shows the guanidinium hydrochloride-induced unfolding of IL-1ra by circular dichroism discussed in Example 6.

Equilibrium guanidinium hydrochloride (GuHCl)-induced unfolding was performed as follows. For far-UV circular dichroism studies, 1-1.5 ml samples of 0.86 mg/ml IL-1ra and various concentrations of GuHCl (between about 0 and 5M) were wrapped in foil to protect them from light and incubated overnight (>12 hours) at room temperature. The circular dichroism at 230 nm was then determined for each sample at 23° C. FIG. 11 shows the circular dichroism signal at 230 nm for IL-1ra incubated in various concentrations of GuHCl. The data were plotted and the unfolding curve was fitted to the 3-state model, native state <-> intermediate state <-> unfolded state. In this model, m1, $C_{m1}$, "ns", which is the slope of the native state baseline, and "is", which is the slope of the intermediate state baseline, were constrained. The constrained values of m1 and $C_{m1}$ for GuHCl-induced unfolding were determined substantially as described above for urea-induced unfolding. "Ns" and "is" were constrained to be greater than zero. Those parameters were constrained because far-UV CD cannot distinguish between the native and the intermediate states. As shown in FIG. 11, IL-1ra underwent a global unfolding transition between about 1 and 2 M GuHCl in this experiment.

Figure 12:
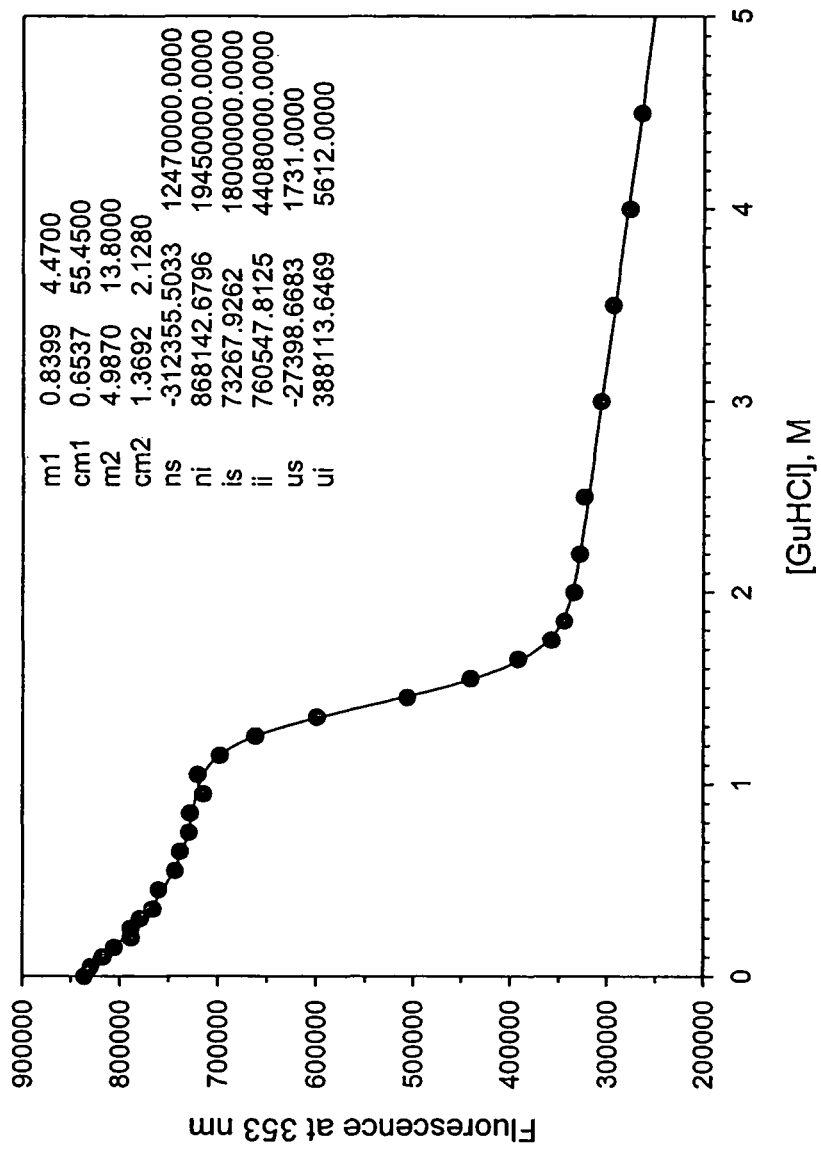
FIG. 12 shows the guanidinium hydrochloride-induced unfolding of IL-1ra by intrinsic fluorescence discussed in Example 6.

For fluorescence studies, 1-1.5 ml samples of 0.086 mg/ml IL-1ra and various concentrations of GuHCl (between about 0 and 5M) were wrapped in foil to protect them from light and incubated overnight (>12 hours) at room temperature. FIG. 12 shows the intrinsic fluorescence at 353 nm of IL-1ra incubated in various concentrations of urea. The data were plotted and the unfolding curve was fitted to the 3-state model discussed above. No constraints were applied in this experiment. FIG. 12 shows the intrinsic fluorescence at 353 nm of IL-1ra incubated in various concentrations of GuHCl. The data were plotted and the unfolding curve was fitted to the 3-state model discussed above. No constraints were applied in this experiment. As shown in FIG. 12, the fluorescence data suggests the presence of the an unfolding transition between about 0 and 0.6 M GuHCl. Since that transition is not observed in the far-UV CD experiment, it may reflect accumulation of an intermediate state with a native-like secondary structure. That intermediate state may involve more local changes to the structure and/or involve destabilization of surface loops, while the hydrophobic core of IL-1ra may remain substantially unperturbed.

The difference between the fluorescence data for urea-induced unfolding and GuHCl-induced unfolding may result from differential effects of the two denaturants on the intrinsic fluorescence of IL-1ra.

Furthermore, the difference between the CD data and the fluorescence data for each denaturant may be due to the ability of tryptophan intrinsic fluorescence to detect local changes in protein tertiary structure, while CD detects changes in protein secondary structure.

Example 7

Derivatization of IL-1ra with Methyl Acetyl Phosphate (MAP)

In certain embodiments, methyl acetyl phosphate (MAP) acetylates lysine residues and the N-terminal amines of polypeptides. MAP was prepared as described in Kluger et al. (1980) *J. Org. Chem.*, 45: 2723. The identity of the product was confirmed by NMR and mass spectrometry.

IL-1ra was derivatized with MAP in the presence of citrate or phosphate as follows. For the derivitization in the presence of citrate, 20 µl of MAP (10 mM stock in water) and 20 µl IL-1ra (10 mM stock in CSE) were added to 160 µl of 10 mM citrate, pH 6.5 in an HPLC vial. The reaction was incubated at 37° C. and 25 µl aliquots were taken using an HPLC autosampler at 0, 45, 90, 135, 180, 225, and 270 minutes. Each aliquot was analyzed by reverse-phase HPLC using an Agilent 110 HPLC equipped with a Jupiter 5u C4 300A reverse-phase HPLC column (4.6×250 mm, Phenomenex, Torrance, Calif.), an on-line UV detector and a temperature-controlled 100-well sample tray set at 37° C. The flow rate was set at 1 ml/min and the column was maintained at a temperature of 50° C. The column was pre-equilibrated for 15 min (flow rate 1 ml/min) with 65% buffer A (0.1% trifluoroacetic acid (TFA) in water) and 35% buffer B (90% acetonitrile, 0.1% TFA in water). After loading, the analytes were eluted using a gradient ramping from 35% to 50% buffer B (90% acetonitrile, 0.1% TFA in water) over 25 minutes.

For derivatization in the presence of phosphate, 20 µl of MAP (10 mM stock in water) and 20 µl IL-1ra (10 mM stock in CSE) were added to 160 µl of 10 mM phosphate, pH 6.5 in an HPLC vial. The reaction was incubated at 37° C. and 25 µl aliquots were taken using an HPLC autosampler at 0, 45, 90, 135, 180, 225, and 270 minutes. Each aliquot was analyzed by reverse-phase HPLC as described above for derivatization in the presence of citrate.

Figure 13:
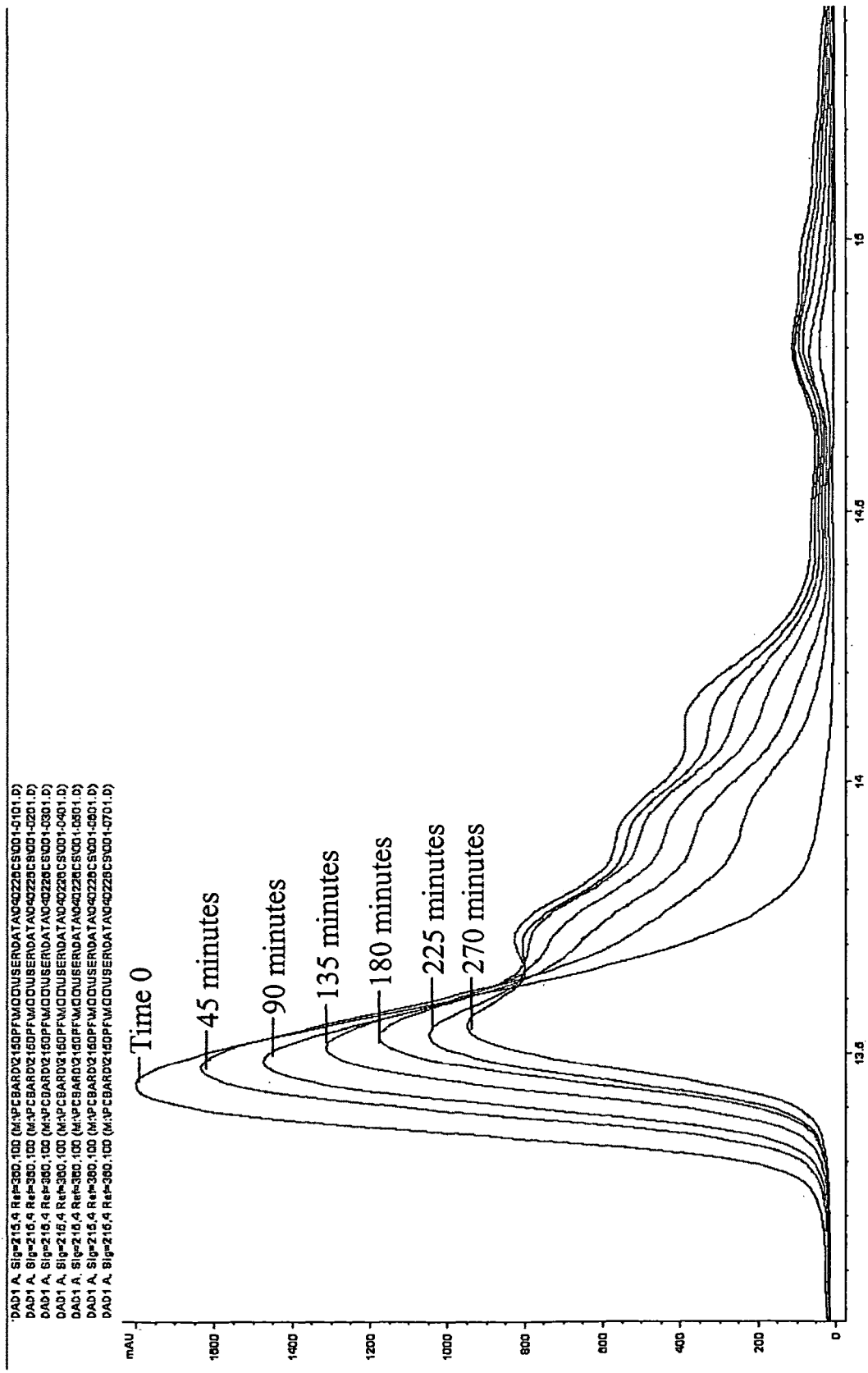
FIG. 13 shows the reverse-phase HPLC of IL-1ra affinity labeled with methyl acetyl phosphate (MAP) in the presence of 10 mM citrate, pH 6.5, discussed in Example 7.
Figure 14:
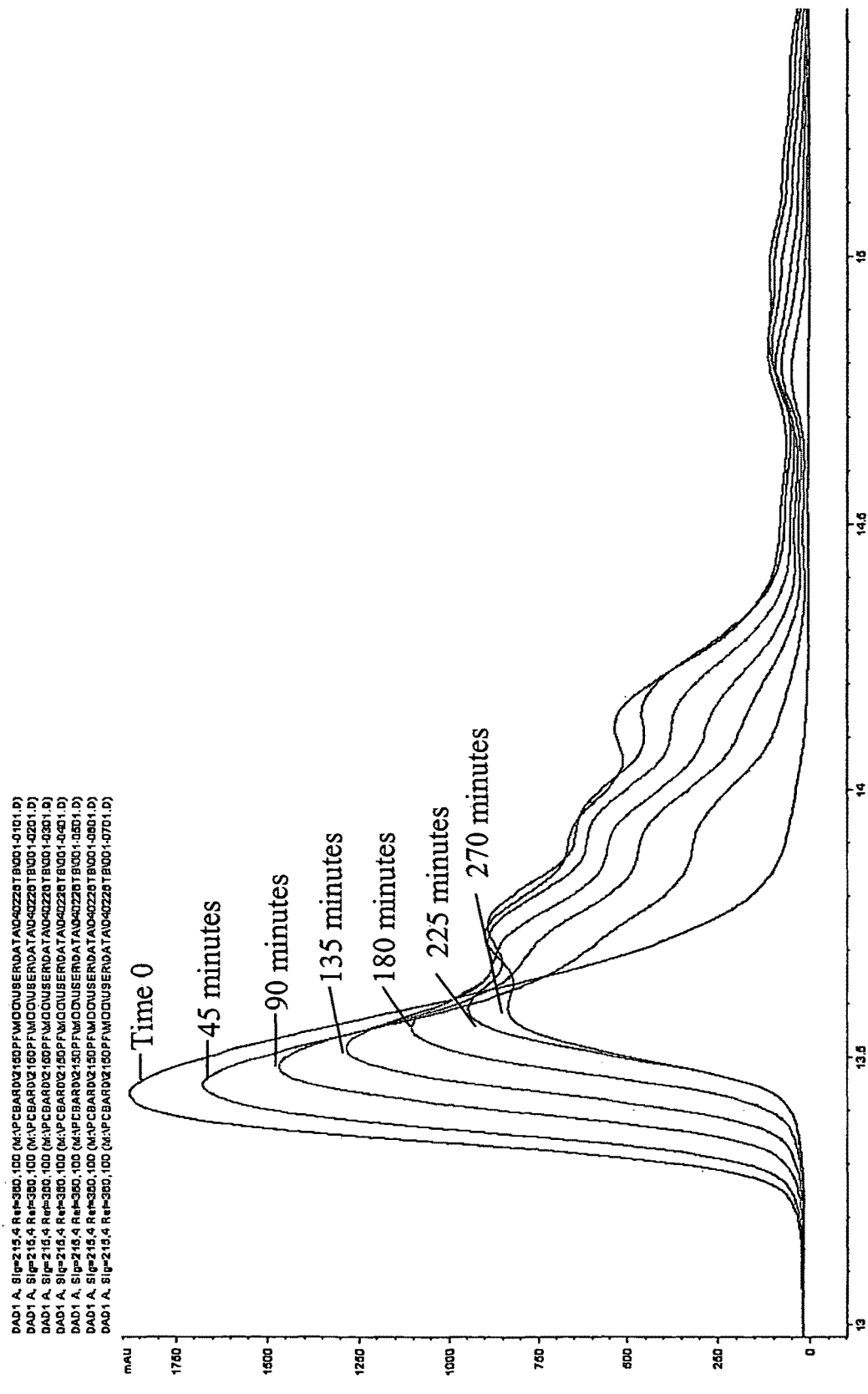
FIG. 14 shows the reverse-phase HPLC of IL-1ra affinity labeled with methyl acetyl phosphate (MAP) in the presence of 10 mM phosphate, pH 6.5, discussed in Example 7.

The results of the derivatization in the presence of citrate are shown in FIG. 13. The results of the derivatization in the presence of phosphate are shown in FIG. 14. Both HPLC profiles reveal four new, weakly-resolved IL-1ra peaks resulting from derivatization with MAP in this experiment.

Figure 15:
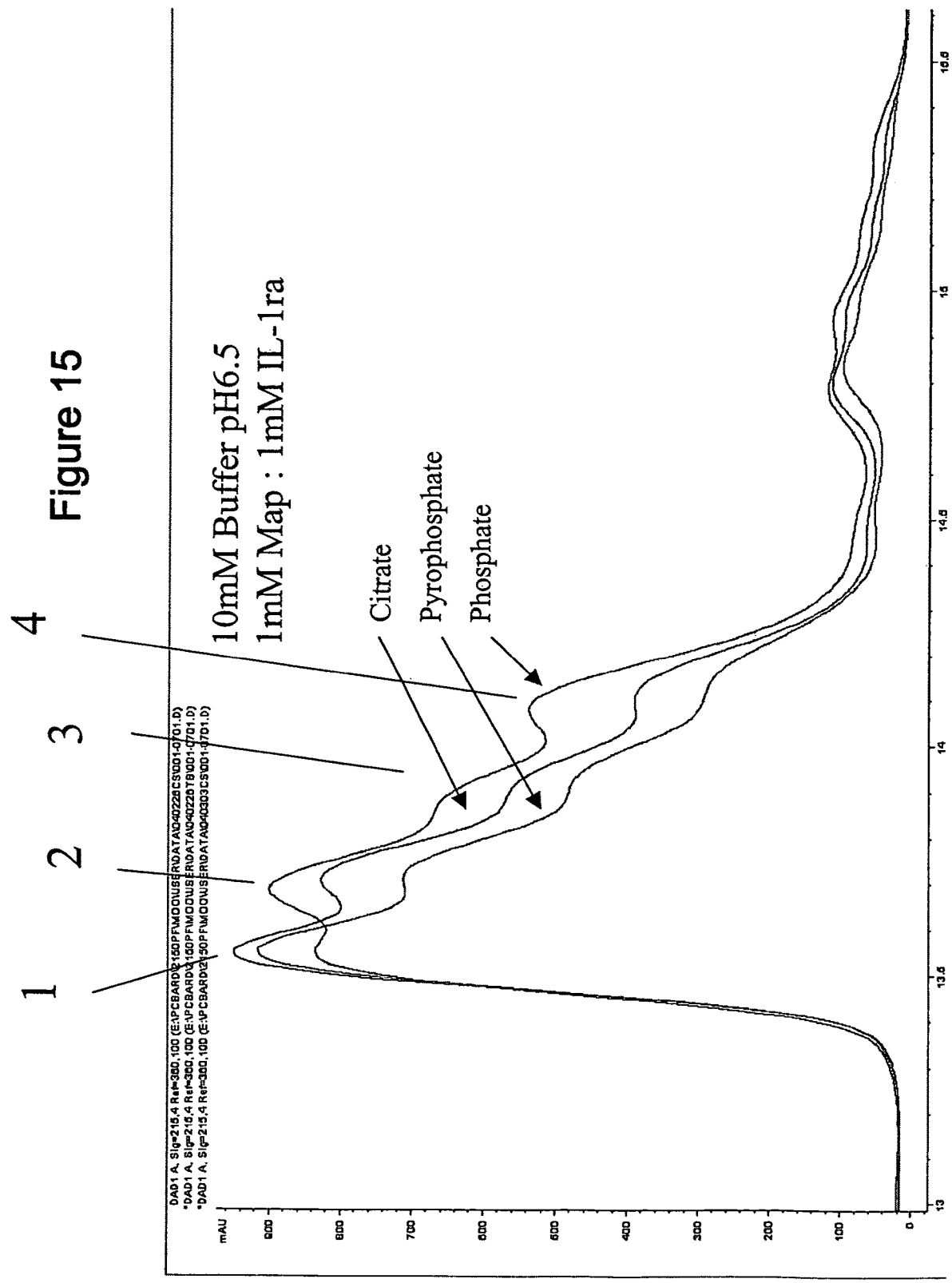
FIG. 15 shows the overlay of the reverse-phase HPLC profiles of IL-1ra affinity labeled with methyl acetyl phosphate for 4.5 hours (270 minutes) in the presence of 10 mM citrate, pH 6.5, 10 mM phosphate, pH 6.5, or 10 mM pyrophosphate, pH 6.4, discussed in Example 7. Four weakly resolved peaks are labeled as 1, 2, 3, and 4.

IL-1ra was also derivatized with MAP in the presence of 10 mM pyrophosphate, pH 6.4. Twenty µl of MAP (10 mM stock in water) and 20 µl IL-1ra (10 mM stock in CSE) were added to 160 µl of 10 mM pyrophosphate, pH 6.4 in an HPLC vial. The reaction was incubated at 37° C. and 25 µl aliquots were taken using an HPLC autosampler at 0, 45, 90, 135, 180, 225, and 270 minutes. Each aliquot was analyzed by reverse-phase HPLC as described above for derivatization in the presence of citrate. FIG. 15 shows an overlay of the results of reverse-phase HPLC of IL-1ra derivatization with MAP for 4.5 hours (270 minutes) in the presence of citrate, in the presence of phosphate, and in the presence of pyrophosphate. Four weakly resolved peaks were identified in this experiment and are indicated on FIG. 15.

Each of the peaks from the 270 minute time point for derivitazation in the presence of citrate, shown in FIG. 15, was further analyzed in order to determine the identity of each, as follows. The four major peaks were collected from the HPLC run discussed above. The samples were concentrated on a SpeedVac to 5-10 µl final volume. Ninety µl of digest buffer (50 mM tris, 0.8 M guanidinium-HCl, pH 8.0) was then added to each sample, followed by 10 µl of endoproteinase lys-C (1 µg in 10 µl digest buffer). The samples were incubated at 37° C. for 16 hours. The resulting peptides were analyzed by LC-MS/MS using an Agilent 110 HPLC equipped with an on-line MS detection with a Finnegan ion trap. The HPLC column used was a Jupiter 5u C18 100A reverse-phase HPLC column (2×150 mm, Phenomenex, Torrance, Calif.). The flow rate was set at 0.2 ml per minute and the column was maintained at a temperature of 50° C. The column was pre-equilibrated for 22 minutes with 98% buffer A ((0.1% TFA in water) and 2% buffer B (90% acetonitrile, 0.1% TFA in water). After loading, analytes were eluted from the HPLC column using a gradient ramping from 2% to 45% buffer B over 50 minutes. Ten percent of the eluent from the HPLC column was subjected to to MS analysis. The presence of an additional acetyl group on a peptide resulted in an increase of 42 m/t on the MS profile relative to unmodified peptide. The identity of the detected peptides and. the specific amino acid residues that were modified was verified by MS/MS.

The IL-1ra polypeptide of peak 1 appeared to be derivatized at its N-terminal amine only. The IL-1ra polypeptide of peak 2 appeared to be derivatized at its N-terminal amine and at lysine-6. The IL-1ra polypeptide of peak 3 appeared to be derivatized at its N-terminal amine, at lysine-6, and at lysine-93. Finally, the IL-1ra polypeptide of peak 4 appeared to be derivatized at its N-terminal amine, at lysine-6, at lysine-93, and at lysine-96.

The level of derivatization at all positions except for the N-terminal amine appeared to be greater in the presence of phosphate than in the presence of citrate or pyrophosphate. These results suggest that citrate and/or pyrophosphate may protect the positively-charged lysine groups in IL-1 ra from derivatization with MAP better than phosphate. These results may suggest that citrate and/or pyrophosphate has a stronger affinity for the positively-charged lysine residues than does phosphate.

Figure 16:
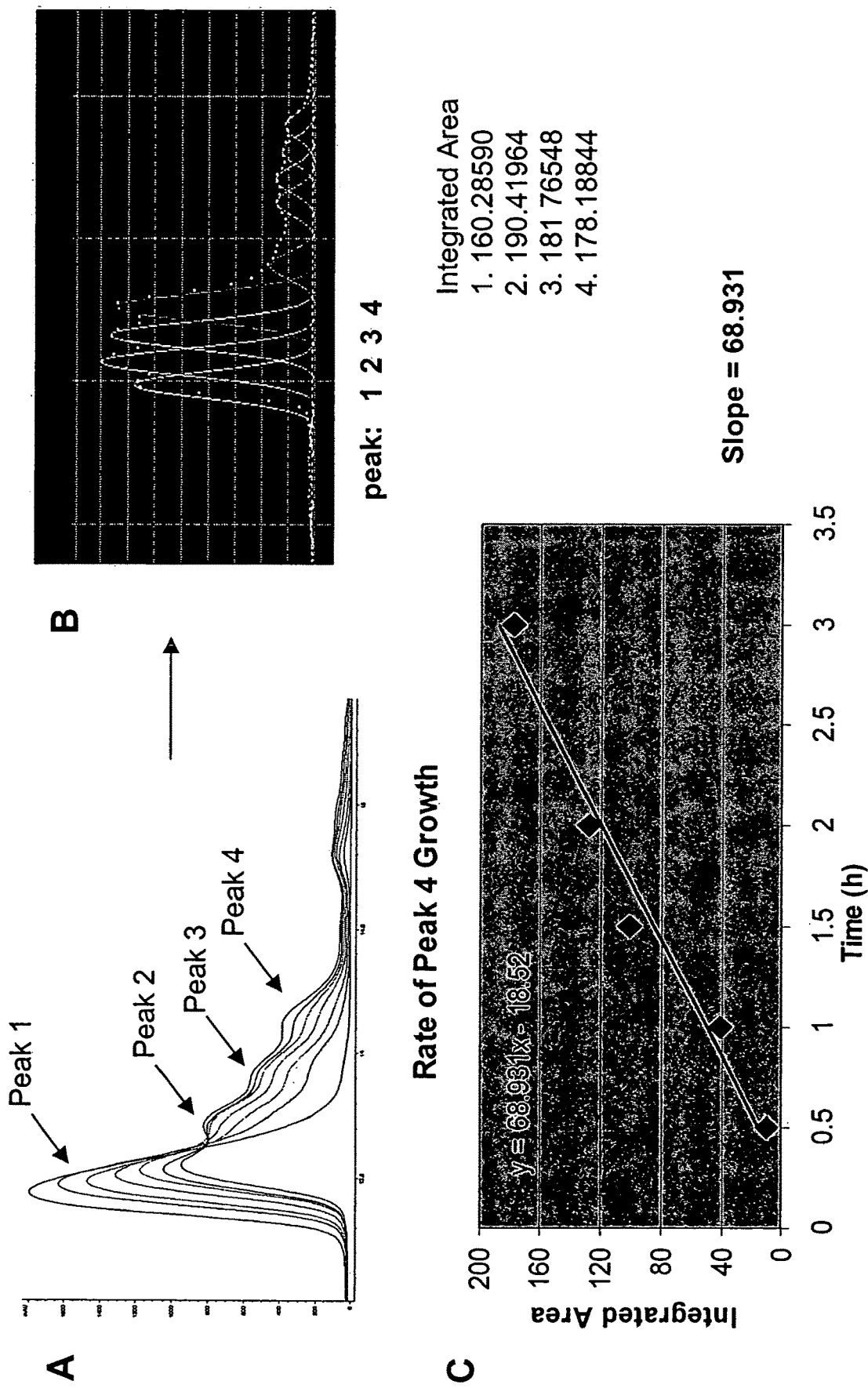
FIG. 16 shows the rate of derivatization of IL-1ra with methyl acetyl phosphate in the presence of 10 mM citrate, pH 6.5, discussed in Example 7.

The rate of derivatization of IL-1ra with MAP was determined using the data shown in FIG. 13 (and reproduced in FIG. 16A) for IL-1ra derivatization in the presence of citrate. In particular, each chromatogram from FIG. 16A was deconvoluted using PeakFit™ (Systat Software Inc.). The area under the each of the deconvoluted peaks (peaks 1-4) at each time point (0, 45, 90, 135, 180, 225, and 270 minutes) was then integrated. An exemplary deconvoluted profile for one time point is shown in FIG. 16B. Deconvoluted peaks 1-4 are labeled on FIG. 16B and the integrated area under each one is shown below. Peak 1 had an integrated area of 160.28590. Peak 2 had an integrated area of 190.41964. Peak 3 had an integrated area of 181.76548. Peak 4 had an integrated area of 178.18844. The integrated area of deconvoluted peak 4 at time points 0, 45, 90, 135, 180 minutes was then plotted against the incubation time of the reaction that produced that peak. That plot is shown in FIG. 16C. The resulting line has a slope of 68.931 hour$^{-1}$.

Figure 17:
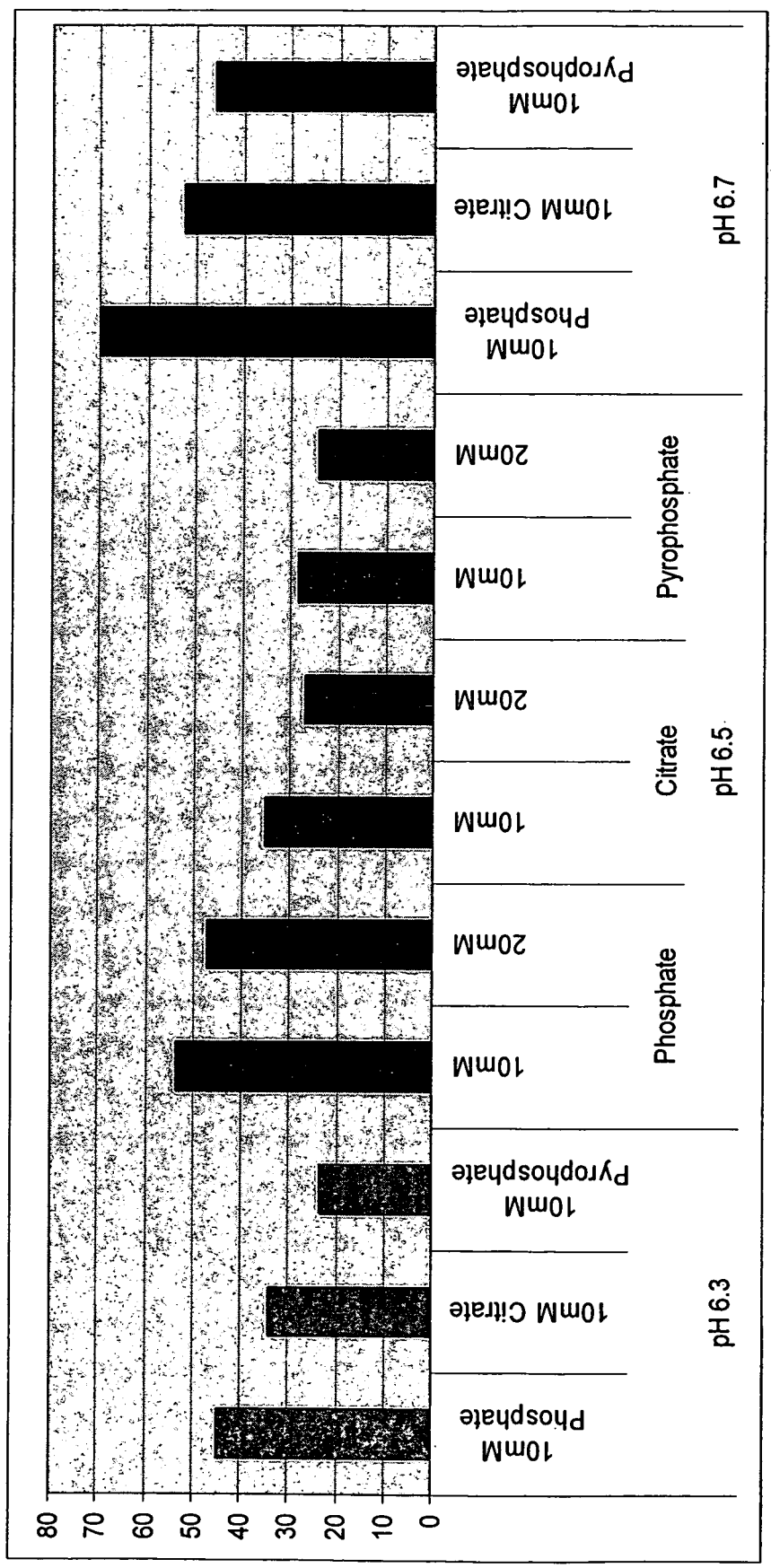
FIG. 17 shows a comparison of the rates of derivatization of IL-1ra with MAP in the presence of various buffers at various pH, discussed in Example 7.

The rate of derivatization of IL-1ra with MAP was then calculated for various experiments in the presence of various buffers and at various pHs, according to the methods discussed above. The various rates were then plotted on a bar chart, shown in FIG. 17. Specifically, the rate of derivatization of IL-1ra with MAP was determined in the presence of 10 mM phosphate, pH 6.3; 10 mM citrate, pH 6.3; 10 mM pyrophosphate, pH 6.3; 10 mM phosphate, pH 6.5; 20 mM phosphate, pH 6.5; 10 mM citrate, pH 6.5; 20 mM citrate, pH 6.5; 10 mM pyrophosphate, pH 6.5; 20 mM pyrophosphate, pH 6.5; 10 mM phosphate, pH 6.7; 10 mM citrate, pH 6.7; and 10 mM pyrophosphate, pH 6.7.

At each pH, the rate of derivatization of IL-1ra with MAP was slower in citrate or pyrophosphate buffer than it was in phosphate buffer. See FIG. 17. Moreover, the rate of derivatization in the presence of 20 mM citrate or pyrophosphate was slower than the rate of derivatization in the presence of 10 mM citrate or pyrophosphate. These results suggest that citrate and/or pyrophosphate may protect the lysine residues of IL-1ra from derivatization with MAP more effectively than does phosphate. Thus, the rate of derivatization of IL-1ra with MAP is slower in the presence of citrate buffer or pyrophosphate buffer than it is in the presence of phosphate buffer.

Figure 18:
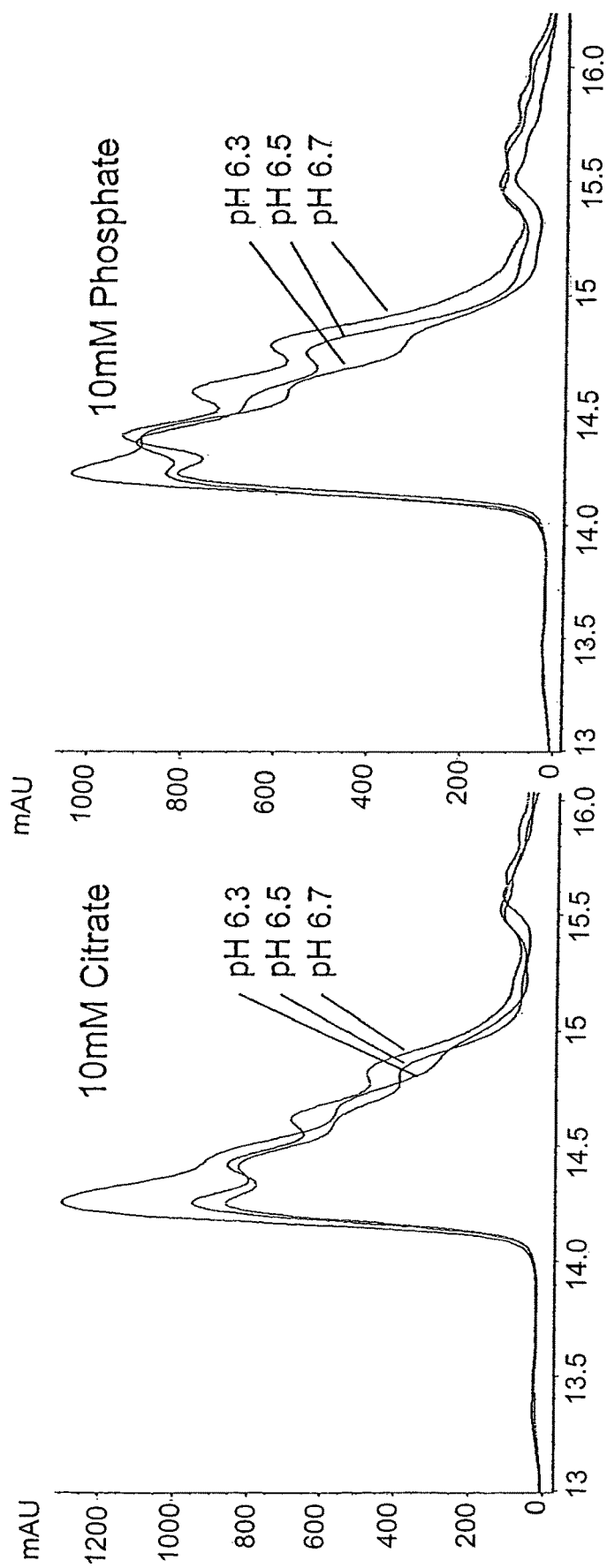
FIG. 18 shows the overlay of the reverse-phase HPLC profiles of IL-1ra affinity-labeled with methyl acetyl phosphate for 5.5 hours in the presence of 10 mM citrate or 10 mM phosphate at various pH levels, discussed in Example 7.

Finally, IL-1ra was also derivatized with MAP in the presence of 10 mM citrate at pH 6.3, pH 6.5, or pH 6.7; or in the presence of 10 mM phosphate, pH 6.3, pH 6.5, or pH 6.7, for 5.5 hours, according to the methods discussed above. FIG. 18 shows an overlay of the results of reverse-phase HPLC of IL-1ra derivatization with MAP for 5.5 hours in the presence of each of those buffers. That figure shows that IL-1ra is derivatized to a greater extent in the presence of phosphate than in the presence of citrate at all pH levels tested. Those results suggest that citrate may protect the lysine residues of IL-1ra from derivatization with MAP more effectively than does phosphate.

The data shown in FIG. 18 also suggest that IL-1ra is derivatized to a greater extent as the pH is increased.

Example 8

IL-1ra Aggregation in the Presence of Various Concentrations of Phosphate

Ten ml of IL-1ra stock (220 mg/ml in CSE) was dialyzed at 4° C. for 48 hours against a total of 8 L (2 L with three buffer changes of 2 L each) 10 mM phosphate, 100 mM NaCl, pH 6.5. The IL-1ra concentration was adjusted to 167 mg/ml with 10 mM phosphate, 100 mM NaCl, pH 6.5. A 1 M stock of phosphate was prepared by dissolving an appropriate amount of sodium phosphate into the 10 mM phosphate, pH 6.5, 100 mM NaCl. Twenty mM, 60 mM, 110 mM, 210 mM, 310 mM, 410 mM, 510 mM, 610 mM, 710 mM, 810 mM, 910 mM, and 1 M working stock solutions of phosphate, pH 6.5 were made from the 1 M stock by diluting with 10 mM phosphate, pH 6.5, 100 mM NaCl.

Figure 19:
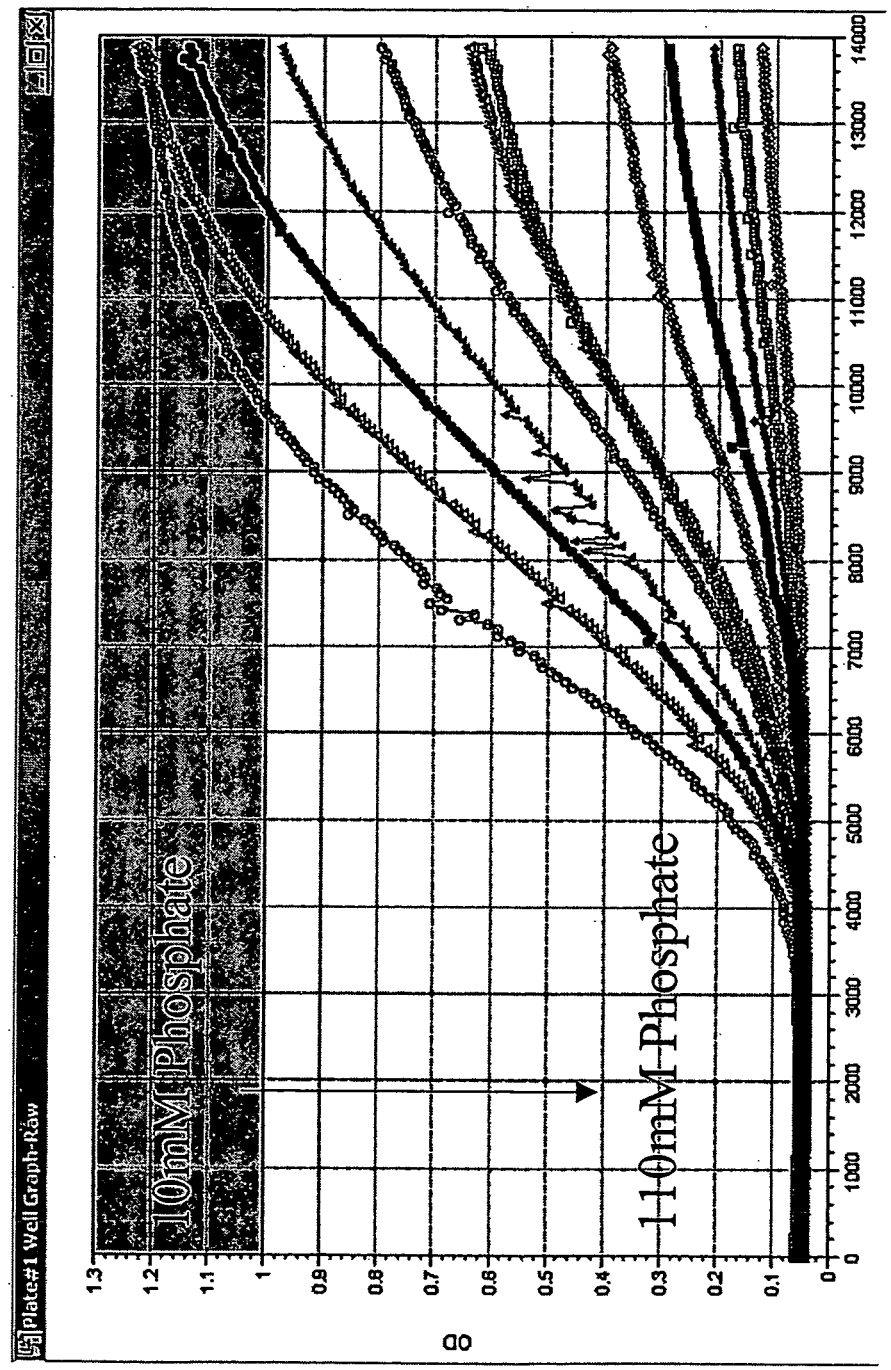
FIG. 19 shows the IL-1ra wild-type protein aggregation profile over time in various concentrations of phosphate in a buffer with 100 mM NaCl, pH 6.5, discussed in Example 8.

Aggregation of IL-1ra in various concentrations of phosphate was measured using a 96-well glass plate (Zissner) and a temperature-controlled plate reading spectrophotometer, SpectraMax Plus (Molecular Devices). One hundred and eighty microliters of the 167 mg/ml ll-1ra stock solution was added to each well. Twenty µl of a phosphate working stock solution was then added to each well (one working stock per well). The final concentration of phosphate in the wells was 0 mM, 2 mM, 6 mM, 11 mM, 21 mM, 31 mM, 41 mM, 51 mM, 61 mM, 71 mM, 81 mM, 91 mM, 100 mM. The plate was incubated in the spectrophotometer at 39° C. and the optical density was measured at 405 nm every 1 minute. FIG. 19 shows the optical density at 405 nm plotted as a function of time for each concentration of phosphate for this experiment. The data in FIG. 19 suggests that the extent of aggregation of IL-1ra decreases with increasing concentration of phosphate.

Example 9

Measurement of Citrate Binding to IL-1ra

The number of citrate ion binding sites and the $K_d$ of citrate binding to IL-1ra were determined as follows. Solutions of 1 ml of 1 mM IL-1 ra were prepared in buffers having various concentrations of citrate, pH 6.5 by diluting IL-1ra stock (220 mg/ml in CSE) in appropriate buffers. Specifically, 1 ml of 1 mM solutions of IL-1ra in each of 5 mM, 10 mM, and 20 mM citrate, pH 6.5 were prepared. Each solution also contained 70 mM NaCl. Four hundred microliters of each solution was placed in a Microsep™-10 spin column (Pall Corporation; one solution per column). The columns were spun at 18° C. for 35 minutes at 4000×g. After spinning, the IL-1ra remains in the retentate, bound to some of the citrate, while some of the buffer containing unbound citrate passes through the filter as filtrate. After spinning, about half of the solution had passed through the filter as filtrate.

The amount of citrate in each of the retentate and filtrate was determined as follows. Twenty μl of filtrate or retentate was loaded onto a reverse phase HPLC column (Supelcosil™ LC-18 column, 15 cm×4.6 mm, Sigma-Aldrich cat. no. 58985). The flow rate was 1 ml per minute with 0.1 M phosphoric acid as running buffer (isocratic elution). The elution was carried out at room temperature. The amount of citric acid eluted from the column was measured at 215 nm. The concentration of citrate in the sample being assayed (the retentate or filtrate) was then calculated from that measurement (the system was calibrated with 0-10 mM citrate solution standards, pH 6.5).

Figure 20:
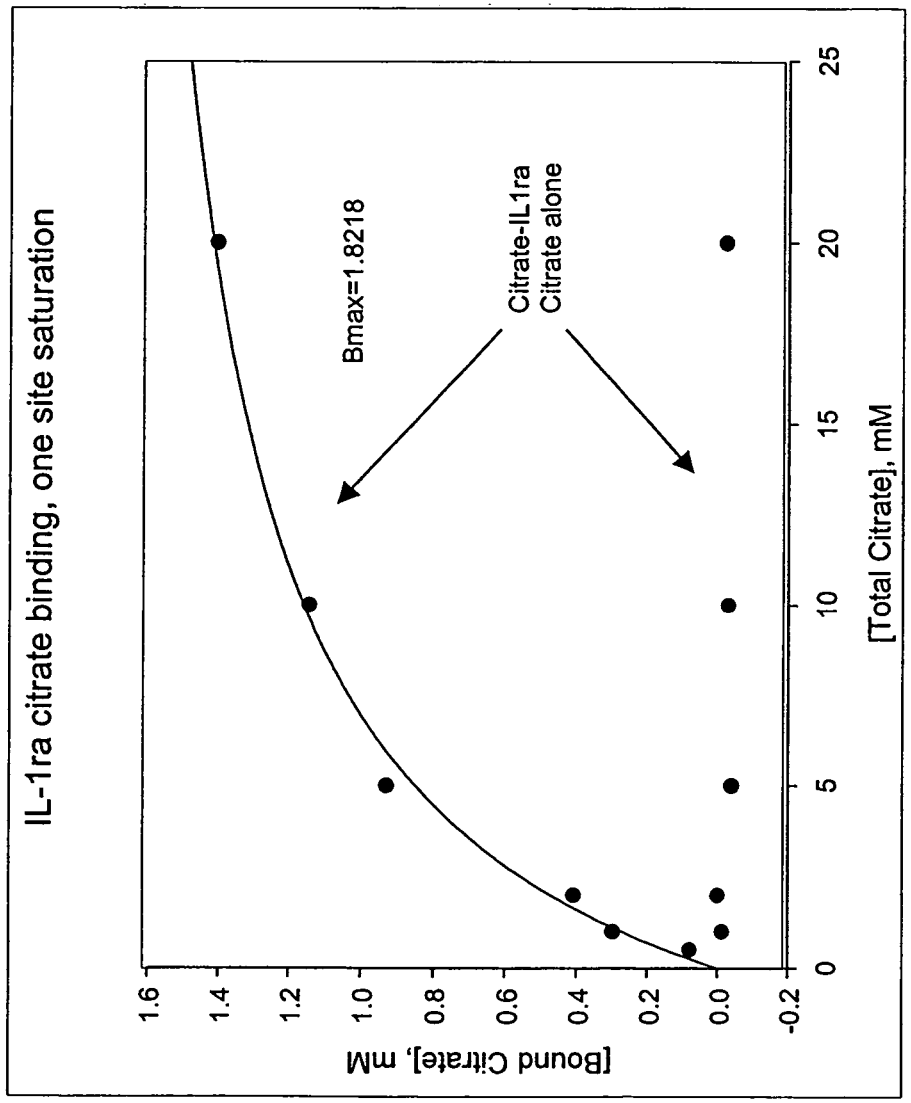
FIG. 20 shows citrate binding to IL-1ra as a function of increasing concentration of citrate, as discussed in Example 9.

FIG. 20 shows a plot of the concentration of citrate bound to IL-1ra (determined as the concentration of citrate in the retentate minus the concentration of citrate in the filtrate) versus the concentration of total citrate in the solution. The maximum concentration of citrate bound, $B_{max}$, was extrapolated from that data to be 1.8218 mM. The data from FIG. 20 was used to create a Scatchard plot in order to determine the $K_d$ for citrate binding to IL-1ra. The $K_d$ was calculated as 3.846 mM for this experiment (data not shown). Furthermore, the number of binding sites for citrate on IL-1ra was determined from the x-intercept on the Scatchard plot. The number of binding sites was 0.94 for this experiment (data not shown). These data suggest that there is one citrate binding site in IL-1ra.

Example 10

Competition for the IL-1ra Anion Binding Site

Competition for the citrate binding site on IL-1ra by pyrophosphate was determined as follows. Four hundred microliters of a solution containing 1 mM IL-1ra, 10 mM citrate, pH 6.5, 70 mM NaCl, and a test concentration of pyrophosphate was placed in a Microsep™-10 spin columns (Pall Corporation) and spun at 18° C. for 35 minutes at 4000×g. The concentrations of pyrophosphate tested were 0 mM, 5 mM, 10 mM, and 20 mM. After spinning, about half of the solution passed through the filter as filtrate, while the remaining solution remained above the filter as retentate. The IL-1ra remains in the retentate, bound to some of the citrate and/or pyrophosphate, while some of the buffer containing unbound citrate and pyrophosphate will pass through the filter as filtrate. The concentration of citrate in both the retentate and the filtrate was determined as discussed above in Example 9. Competition for the citrate binding site on IL-1ra by phosphate was determined as described above for pyrophosphate.

Figure 21:
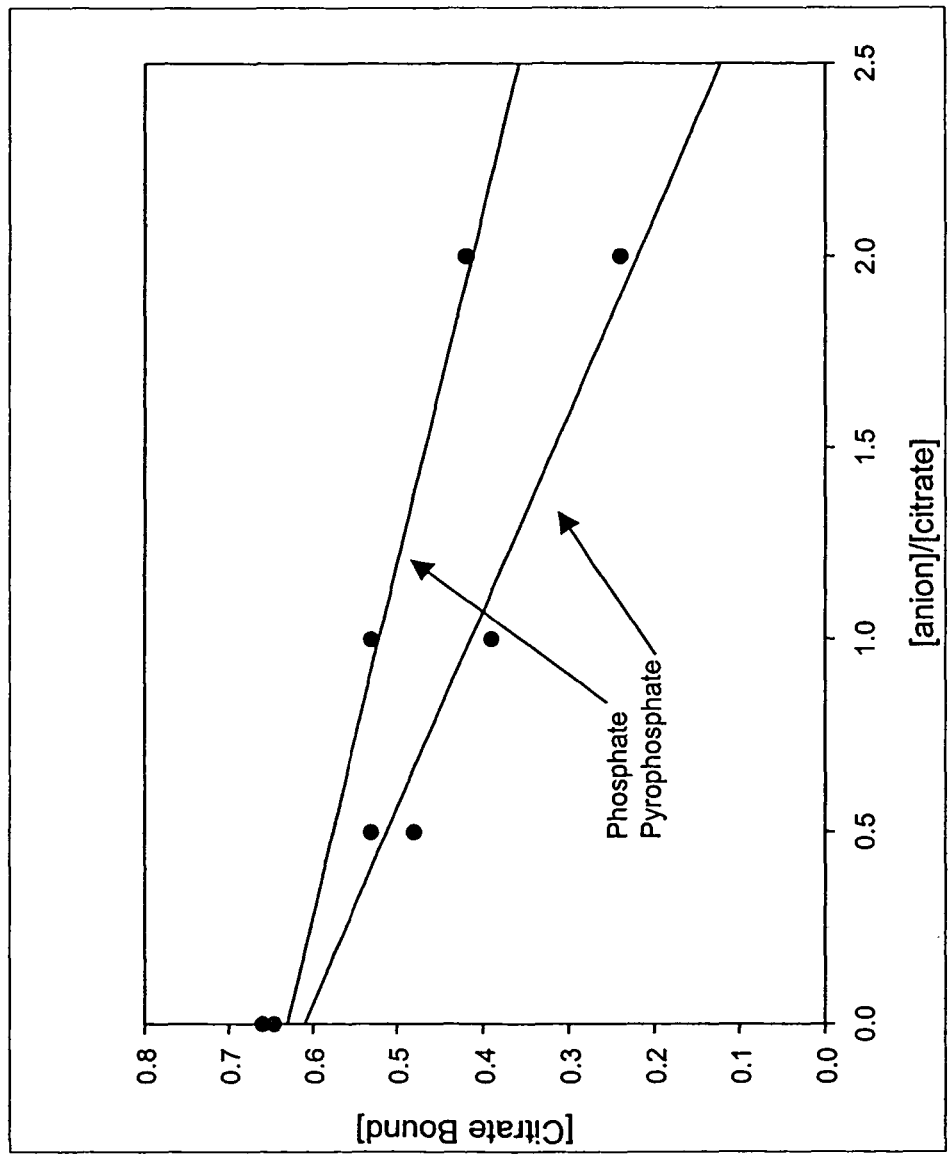
FIG. 21 shows competition for citrate binding to IL-1ra by increasing concentrations of pyrophosphate or phosphate, as discussed in Example 10.

FIG. 21 shows a plot of the concentration of citrate bound by IL-1ra versus the ratio of the total concentration of competing anion (pyrophosphate or phosphate) to the total concentration of citrate in the solution. The data suggest that pyrophosphate is more effective at competing with citrate for the citrate binding site on IL-1ra than is phosphate. Because both pyrophosphate and phosphate appear to be capable of competing for the IL-1ra binding site (i.e., the site is not specific for citrate), we refer to the citrate binding on IL-1ra site as the anion binding site.

From the data shown in FIG. 21, the $K_d$ for pyrophosphate binding to the anion binding site on IL-1ra was determined using the following calculations. See, e.g., Stinson and Holbrook, *Biochem. J.* (1973) 131: 719-728. The competition between citrate and pyrophosphate binding can be expressed as two separate equilibria:

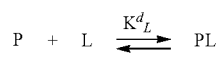

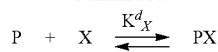

Where P=protein, which is IL-1ra in this case; L=ligand, which is citrate in this case; and X=competing anion, which is pyrophosphate in this case. $K^d_L$ is the $K_d$ for ligand binding to protein and is equal to the concentration of P (free protein) times the concentration of L (free ligand), divided by the concentration of PL (protein bound to ligand). $K^d_X$ is the $K_d$ for competitive anion binding to protein and is equal to the concentration of P (free protein) times the concentration of X (free competing anion), divided by concentration of PX (protein bound to competing anion).

The apparent, or observed $K_d$ of citrate ($K^d_L$app) can be expressed as follows:

$$K^d_L app = \frac{(L_{free})[(P_{free}) + (PX)]}{(PL)}$$

Where $L_{free}$ is the concentration of free ligand (citrate), $P_{free}$ is the concentration of free protein (IL-1ra), PX is the concentration of protein bound to competitive anion (pyrophosphate), and PL is the concentration of protein bound to ligand. By replacing the (PX) term with $(X_{free})(P_{free})/K^d_X$, which is derived from the equilibrium equation shown above, the expression for $K^d_L$app can be reduced to:

$$K^d_L app = K^d_L[1+(X_{free}/K^d_X)]$$

Thus, if $K^d_L$app is plotted versus $X_{free}$, the y-intercept will be equal to $K^d_L$ and the slope will be equal to $K^d_L/K^d_X$. Rearranging, $K^d_X$ will be equal to the y-intercept divided by the slope.

$K^d_L$app for citrate binding is calculated at each concentration of competing anion as the concentration of free protein (IL-1ra) times the concentration of free ligand (citrate), divided by the concentration of bound ligand (citrate bound to IL-1ra). The concentration of free protein is calculated to be the total concentration of protein in the sample minus the concentration of bound protein (which is equal to the concentration of bound ligand). $X_{free}$, or the concentration of free competing anion, is equal to the total concentration of competing anion minus the change in the concentration of bound ligand (citrate bound to IL-1ra) as the total concentration of competing anion is increased (i.e., as citrate is replaced at the IL-1ra anion binding sites by the competing anion). In other words, $X_{free} = X_{total} - \Delta X_{bound}$ as $X_{total}$ is increased.

Figure 22:
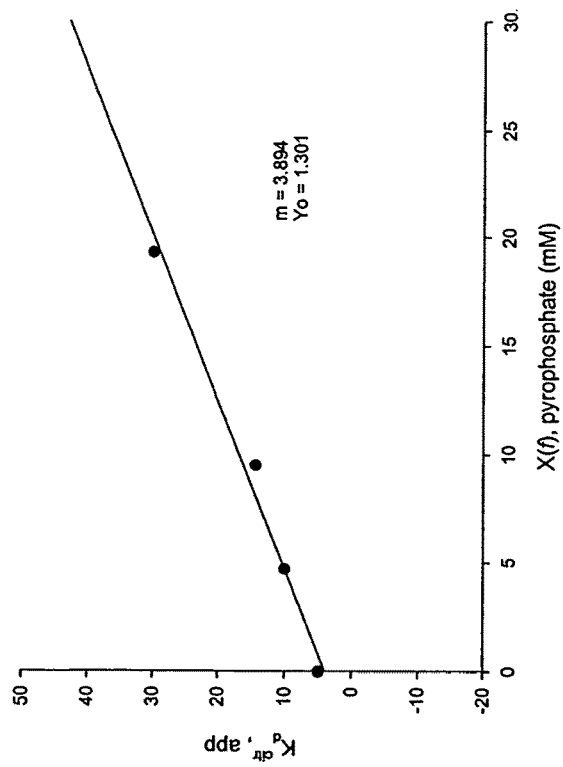
FIG. 22 shows a plot of the $K^d_L\mathrm{app}$ for citrate binding to IL-1ra as a function of pyrophosphate concentration in the solution, as discussed in Example 10. The $K^d_X$ for pyrophosphate binding to the anion-binding site of IL-1ra was calculated to be 2.994 mM.

FIG. 22 shows a plot of $K^d_L$app for citrate versus the amount of free pyrophosphate, as calculated using the data from FIG. 20 and the calculations discussed above. The $K^d_X$ for pyrophosphate was calculated as 2.994 mM for this experiment. As stated above, the y-intercept should be equal to $K^d_L$, which is the $K_d$ of citrate. In this experiment, the $K^d_L$ was 3.894 mM, which agrees well with the previous experimental determination of the $K_d$ for citrate binding to IL-1ra, 3.846 mM, discussed in Example 9.

A similar plot (data not shown) was created for the phosphate data shown in FIG. 21. In this experiment, the $K^d_X$ for phosphate was calculated to be 12.641 mM. The $K^d_L$ for citrate, as determined from the y-intercept of the plot for this experiment (data not shown), was 4.996 mM.

These data suggest that citrate and pyrophosphate have lower $K_d$s for the anion binding site of IL-1ra. Furthermore, pyrophosphate may have a slightly lower $K_d$ than citrate for than anion binding site. The lower $K_d$s seen in this experiment correlate with the greater ability of pyrophosphate and citrate to reduce aggregation of IL-1ra, as shown in Examples 2 and 4.

What is claimed is:

1. A method of reducing aggregation of an aggregating interleukin-1 receptor antagonist (IL-1ra) in an aqueous composition comprising
   incubating the aqueous composition comprising the IL-1ra with at least one accessory molecule at a concentration sufficient to reduce aggregation of the IL-1ra for at least two hours at 25 to 45° C., and
   determining reduced aggregation of the IL-1ra in the aqueous composition by measuring the optical density at 405 nm of the aqueous composition after at least two hours of incubation at 30 to 45° C., wherein the optical density of the aqueous composition comprising the IL-1ra is less than 60% of the optical density of an aqueous composition comprising the IL-1ra without incubating with the accessory molecule, and
   wherein the at least one accessory molecule is selected from the group consisting of (1) a sugar at a concentration of from 1 to 2 percent, wherein the sugar is sucrose, glycerol, or sorbitol, (2) a multiple-charge anion, wherein the multiple-charge anion is 1 to 20 mM pyrophosphate or 1 to 20 mM citrate, and (3) a lysine-reactive accessory molecule or an arginine-reactive accessory molecule, selected from the group consisting of the three compounds from 6-(N-(7-nitrobenz-2-oxa-1,3-diazol-4-yl)amino)hexanoic acid (NBD-X), methyl acetyl phosphate (MAP), and citraconic anhydride.

2. The method of claim 1, wherein the at least one accessory molecule is a sugar, wherein the sugar is sucrose, glycerol, or sorbitol.

3. The method of claim 1, wherein the at least one accessory molecule is a multiple-charge anion, wherein the multiple-charge anion is 1 to 20 mM pyrophosphate or 1 to 20 mM citrate.

4. The method of claim 3, wherein said multiple-charge anion is 1 to 20 mM pyrophosphate.

5. The method of claim 3, wherein said multiple-charge anion is 1 to 20 mM citrate.

6. The method of claim 1, wherein the at least one accessory molecule is selected from a lysine-reactive accessory molecule and an arginine-reactive accessory molecule, wherein the lysine-reactive accessory molecule and the arginine-reactive accessory molecule are selected from the group consisting of the three compounds from 6-(N-(7-nitrobenz-2-oxa-1,3-diazol-4-yl)amino)hexanoic acid (NBD-X), methyl acetyl phosphate (MAP), and citraconic anhydride, thereby forming an IL-1ra derivatized with NBD-X, MAP, or citraconic anhydride.

7. The method of claim 1, wherein the step of determining reduced aggregation of the IL-1ra in the aqueous composition comprises measuring the optical density at 405 nm of the aqueous composition after at least two hours of incubation at 35 to 45° C.

\* \* \* \* \*

SEQUENCE LISTING

<160> NUMBER OF SEQ ID NOS: 6

<210> SEQ ID NO 1
<211> LENGTH: 600
<212> TYPE: DNA
<213> ORGANISM: Homo sapiens

<400> SEQUENCE: 1

| | | | | | |
|---|---|---|---|---|---|
| gaattccggg | ctgcagtcac | agaatggaaa | tctgcagagg | cctccgcagt | cacctaatca | 60 |
| ctctcctcct | cttcctgttc | cattcagaga | cgatctgccg | accctctggg | agaaaatcca | 120 |
| gcaagatgca | agccttcaga | atctgggatg | ttaaccagaa | gaccttctat | ctgaggaaca | 180 |
| accaactagt | tgctggatac | ttgcaaggac | caaatgtcaa | tttagaagaa | aagatagatg | 240 |
| tggtacccat | tgagcctcat | gctctgttct | tgggaatcca | tggagggaag | atgtgcctgt | 300 |
| cctgtgtcaa | gtctggtgat | gagaccagac | tccagctgga | ggcagttaac | atcactgacc | 360 |
| tgagcgagaa | cagaaagcag | gacaagcgct | tcgccttcat | ccgctcagac | agtggcccca | 420 |
| ccaccagttt | tgagtctgcc | gcctgccccg | gttggttcct | ctgcacagcg | atggaagctg | 480 |
| accagcccgt | cagcctcacc | aatatgcctg | acgaaggcgt | catggtcacc | aaattctact | 540 |
| tccaggagga | cgagtagtac | tgcccaggcc | tgctgttcca | ttcttgcatg | gcaaggactg | 600 |

<210> SEQ ID NO 2
<211> LENGTH: 177
<212> TYPE: PRT
<213> ORGANISM: Homo sapiens

<400> SEQUENCE: 2

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 3
<211> LENGTH: 152
<212> TYPE: PRT
<213> ORGANISM: Homo sapiens

<400> SEQUENCE: 3

```
Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150
```

```
<210> SEQ ID NO 4
<211> LENGTH: 475
<212> TYPE: DNA
<213> ORGANISM: Artificial
<220> FEATURE:
<223> OTHER INFORMATION: coding sequence for anakinra
```

<400> SEQUENCE: 4

```
catatgcgac cgtccggccg taagagctcc aaaatgcagg ctttccgtat ctgggacgtt    60
aaccagaaaa ccttctacct gcgcaacaac cagctggttg ctggctacct gcagggtccg   120
aacgttaacc tggaagaaaa aatcgacgtt gtaccgatcg aaccgcacgc tctgttcctg   180
ggtatccacg gtggtaaaat gtgcctgagc tgcgtgaaat ctggtgacga aactcgtctg   240
cagctggaag cagttaacat cactgacctg agcgaaaacc gcaaacagga caaacgtttc   300
gcattcatcc gctctgacag cggcccgacc accagcttcg aatctgctgc ttgcccgggt   360
tggttcctgt gcactgctat ggaagctgac cagccggtaa gcctgaccaa catgccggac   420
gaaggcgtga tggtaaccaa attctacttc caggaagacg aataatggga agctt         475
```

```
<210> SEQ ID NO 5
<211> LENGTH: 153
<212> TYPE: PRT
<213> ORGANISM: Artificial
<220> FEATURE:
<223> OTHER INFORMATION: anakinra sequence
```

<400> SEQUENCE: 5

```
Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60
```

```
Lys Met Cys Leu Ser Cys Val Lys Ser Gly Asp Glu Thr Arg Leu Gln
65              70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
            115                 120                 125

Asp Gln Pro Val Ser Leu Thr Asn Met Pro Asp Glu Gly Val Met Val
            130                 135                 140

Thr Lys Phe Tyr Phe Gln Glu Asp Glu
145                 150

<210> SEQ ID NO 6
<211> LENGTH: 159
<212> TYPE: PRT
<213> ORGANISM: Artificial
<220> FEATURE:
<223> OTHER INFORMATION: icIL-1ra sequence

<400> SEQUENCE: 6

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
            35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65              70                  75                  80

Asp Glu Thr Arg Leu Gln Leu Glu Ala Val Asn Ile Thr Asp Leu Ser
            85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
            115                 120                 125

Cys Thr Ala Met Glu Ala Asp Gln Pro Val Ser Leu Thr Asn Met Pro
            130                 135                 140

Asp Glu Gly Val Met Val Thr Lys Phe Tyr Phe Gln Glu Asp Glu
145                 150                 155
```